(12) United States Patent
Bhattacharya et al.

(10) Patent No.: US 11,365,202 B2
(45) Date of Patent: Jun. 21, 2022

(54) ANTIMALARIAL COMPOUNDS, PROCESS FOR PREPARATION AND THEIR USE FOR DRUG RESISTANT MALARIA

(71) Applicants: Council of Scientific and Industrial Research, New Delhi (IN); International Centre for Genetic Engineering and Biotechnology (ICGEB), New Delhi (IN)

(72) Inventors: Asish Kumar Bhattacharya, Pune (IN); Eswar Kumar Aratikatla, Pune (IN); Pawan Malhotra, New Delhi (IN); Asif Mohmmed, New Delhi (IN)

(73) Assignees: Council of Scientific and Industrial Research, New Delhi (IN); International Centre for Genetic Engineering and Biotechnology (ICGEB), New Delhi (IN)

( * ) Notice: Subject to any disclaimer, the term of this patent is extended or adjusted under 35 U.S.C. 154(b) by 0 days.

(21) Appl. No.: 17/048,505

(22) PCT Filed: Apr. 16, 2019

(86) PCT No.: PCT/IN2019/050309
§ 371 (c)(1),
(2) Date: Oct. 16, 2020

(87) PCT Pub. No.: WO2019/202609
PCT Pub. Date: Oct. 24, 2019

(65) Prior Publication Data
US 2021/0101907 A1    Apr. 8, 2021

(30) Foreign Application Priority Data

Apr. 16, 2018    (IN) .............................. 201811014401

(51) Int. Cl.
*C07D 493/18* (2006.01)
(52) U.S. Cl.
CPC ................... *C07D 493/18* (2013.01)
(58) Field of Classification Search
CPC .................................................. C07D 493/18
USPC ....................................................... 549/348
See application file for complete search history.

(56) References Cited

U.S. PATENT DOCUMENTS

2012/0101151 A1    4/2012    Gros et al.

FOREIGN PATENT DOCUMENTS

WO    WO-2019202609 A1    10/2019

OTHER PUBLICATIONS

Ajay Singh et al , Selection of Cysteine Protease Inhibitor-resistant Malaria Parasites is accompanied by amplification of Falcipain Genes and alteration in Inhibitors Transport (Year: 2004).*
"International Application No. PCT/IN2019/050309, Article 19 received in IB dated Sep. 9, 2019", (Sep. 9, 2019), 14 pgs.
"International Application No. PCT/IN2019/050309, International Search Report and Written Opinion dated Jul. 9, 2019", (Jul. 9, 2019), 9 pgs.
Alqahtani, Norah, et al., "Synergism between genome sequencing, tandem mass spectrometry and bio-inspired synthesis reveals insights into nocardioazine B biogenesis", Org. Biomol. Chem., 2015, 13, 7177-7192, (Apr. 29, 2015), 7177-7192.
Capela, Rita, et al., "Artemisinin-dipeptidyl vinyl sulfone hybrid molecules: design, synthesis and preliminary SAR for antiplasmodial activity and falcipain-2 inhibition", Bioorg Med Chem Lett. Jun. 15, 2009; 19(12): 3229-3232. doi:10.1016/j.bmcl.2009.04.100, (Jun. 15, 2009), 3229-3232.
Chand, Hemender R., et al., "Diastereoselective Synthesis of β-Ether Derivatives of Artemisinin, an Antimalarial Drug: The Effect of Nitrile on Stereoselectivity", Asian J. Org. Chem. 2016, 5(2), 201-206, (Feb. 2016), 201-206.
Kumar, Amit, et al., "Exploring the role of putative active site amino acids and pro-region motif of recombinant falcipain-2: a principal hemoglobinase of Plasmodium falciparum", Biochemical and Biophysical Research Communications 317(1) (2004) 38-45, (2004), 38-45.

(Continued)

*Primary Examiner* — Niloofar Rahmani
(74) *Attorney, Agent, or Firm* — Schwegman Lundberg & Woessner, P.A.

(57) ABSTRACT

The present invention provides a new artemisinin-dipeptidyl vinyl based compound of Formula (I) or a pharmaceutically acceptable salt thereof and a process for the preparation thereof. The present invention further also provides a pharmaceutical composition comprising compounds of Formula (I) or a pharmaceutically acceptable salt thereof, and a pharmaceutically acceptable carrier, diluent or excipient to treat malaria.

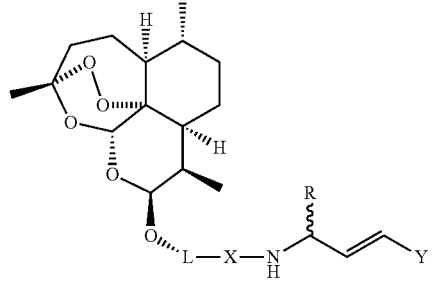

Formula (I)

8 Claims, 1 Drawing Sheet

(56) References Cited

OTHER PUBLICATIONS

Lambros, Chris, et al., "Synchronization of Plasmodium falciparum Erythrocytic Stages in Culture", The Journal of Parasitology, vol. 65, No. 3 (Jun. 1979), pp. 418-420, (Jun. 1979), 418-420.

Maison, Wolfgang, et al., "Optimal N-Caps for N-Terminal Helical Templates: Effects of Changes in H-Bonding Efficiency and Charge", J. Am. Chem. Soc. 2001, 123, 42, 10245-10254 [abstract only], (Sep. 26, 2001), 10245-10254.

Shenai, Bhaskar R., et al., "Characterization of Native and Recombinant Falcipain-2, a Principal Trophozoite Cysteine Protease and Essential Hemoglobinase of Plasmodium falciparum", The Journal of Biological Chemistry, vol. 275, No. 37, Issue of Sep. 15, pp. 29000-29010, 2000, (Sep. 15, 2000), 29000-29010.

Smilkstein, Martin, et al., "Simple and Inexpensive Fluorescence-Based Technique for High-Throughput Antimalarial Drug Screening", Antimicrobial Agents and Chemotherapy, vol. 48, No. 5, May 2004, p. 1803-1806, (May 2004), 1803-1806.

Trager, W., et al., "Human malaria parasites in continuous culture", Science, Vo. 193, Issue 4254, pp. 673-675, (Aug. 20, 1976), 673-675.

Yeung, Shunmay, et al., "Antimalarial Drug Resistance, Artemisinin-based Combination Therapy, and the Contribution of Modeling To Elucidating Policy Choices", Am. J. Trop. Med. Hyg., 71(Suppl 2), 2004, pp. 179-186, (Aug. 2004), 179-186.

\* cited by examiner

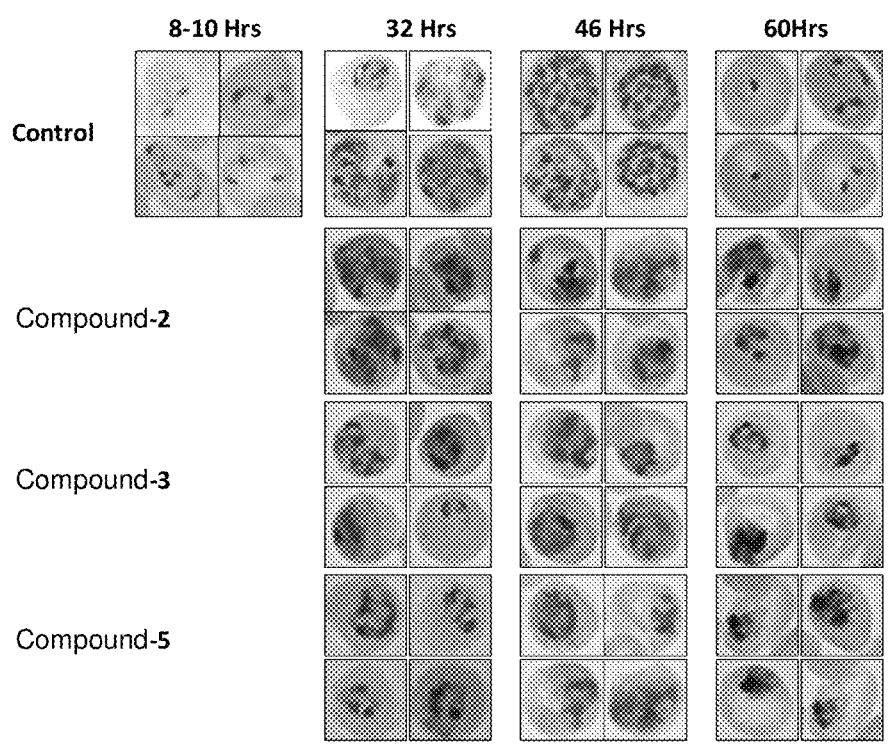

ANTIMALARIAL COMPOUNDS, PROCESS FOR PREPARATION AND THEIR USE FOR DRUG RESISTANT MALARIA

PRIORITY CLAIM TO RELATED APPLICATIONS

This application is a U.S. national stage filing under 35 U.S.C. § 371 from International Application No. PCT/IN2019/050309, filed on 16 Apr. 2019, and published as WO2019/202609 on 24 Oct. 2019, which claims the benefit under 35 U.S.C. 119 to India Application No. 201811014401, filed on 16 Apr. 2018, the benefit of priority of each of which is claimed herein, and which applications and publication are hereby incorporated herein by reference in their entirety.

FIELD OF THE INVENTION

The present invention relates to a new antimalarial compounds and process for the preparation thereof. More particularly, the present invention provides a new artemisinin-dipeptidyl vinyl based compound of Formula (I) or a pharmaceutically acceptable salt thereof and a process for the preparation thereof. The present invention further also relates to an application of the new compounds of Formula (I) or a pharmaceutically acceptable salt thereof to treat malaria.

BACKGROUND AND PRIOR ART OF THE INVENTION

Malaria continues to be major parasitic diseases in tropical and subtropical regions. It is estimated that about 40% of the world's population lives in malaria endemic areas and it cause about 1 million annual mortality globally. The situation is worsened by widespread development of parasite lines resistant to most of the commonly used antimalarials. Falcipains are papain family cysteine proteases, active site residues (Cys, His, Asn) are conserved within the papain family, but falcipains have a unique N-terminal extension acting as a refolding domain, and a C-terminal insert as a hemoglobin (Hb) binding domain. Among the falcipains, four falcipains have been identified so far in the *P. falciparum* genome are falcipain-1 (FP-1), falcipain-2 and -2' (now known as FP-2A and -2B), and falcipain-3 (FP-3). Cysteine proteases (falcipains) of *Plasmodium falciparum* are potential targets for antimalarial chemotherapy, since they have been shown to be involved in important cellular functions such as hemoglobin degradation and invasion/rupture of red blood cells during parasite life cycle.

Artemisinin-based combination therapies (ACTs) for malaria treatment known in the literature. Antimalarial drug resistance, artemisinin-based combination therapy, and the contribution of modeling to elucidating policy choices is reported by Yeung S et al. in *Am J Trop Med Hyg*. 2004 August; 71(2 Suppl):179-86. Further US2012101151 relates to compounds, methods, uses, compositions, combinations, kits and packages for the prevention and/or treatment of parasite infection (e.g., *Plasmodium* parasites) and/or disease (e.g., malaria) based on uses of (a) cystamine, cysteamine, and analogs, derivatives, prodrugs, precursors thereof; an agent capable of inducing their production; and/or salts thereof, and (b) artemisinin and functional derivative, analog, conjugate, metabolite, prodrug or precursor thereof, and/or salts thereof.

Further, artemisinin derived antimalarial drugs clinically being used are either ether derivatives (e.g. arteether, artemether) or water-soluble esters like sodium artesunate or sodium artelinate. However, all these drugs have the same drug targets i.e. they have same mode of action as of the parent compound, artemisinin.

The artemisinin-based combination therapies (ACTs) remains to be only available options for malaria treatment; however recent reports have shown that *Plasmodium falciparum* strains resistance to derivatives of endoperoxide artemisinin are also emerging. Hence, there is urgent need to develop novel antimalarial drugs having diverse mode of action in the parasite.

Therefore the object of the invention is to provide robust drug candidate for treatment of infections due to parasites that have resistance to other antimalarials including artemisinin by employing dual targeting approach.

OBJECTS OF THE INVENTION

The main objective of the present invention is to provide a new artemisinin-dipeptidyl vinyl based compound of Formula (I) or a pharmaceutical acceptable salt thereof.

Another objective of the present invention is to provide a process for the synthesis of a new artemisinin-dipeptidyl vinyl based compound of Formula (I) or a pharmaceutically acceptable salt thereof.

Yet another objective of the present invention is to provide a pharmaceutical composition comprising an artemisinin-dipeptidyl vinyl based compound of Formula (I), or a pharmaceutically acceptable salt thereof and a pharmaceutically acceptable carrier, diluent or excipient for treating malarial infection in a subject in need thereof.

SUMMARY OF THE INVENTION

The present invention provides a new artemisinin-dipeptidyl vinyl based compounds of Formula (I) or a pharmaceutically acceptable salt thereof.

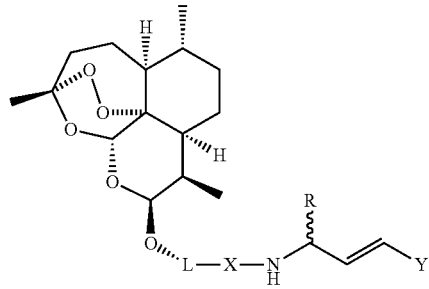

Formula (I)

Wherein, 'L' is Linker selected from group consisting of

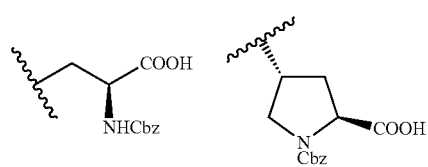

-continued

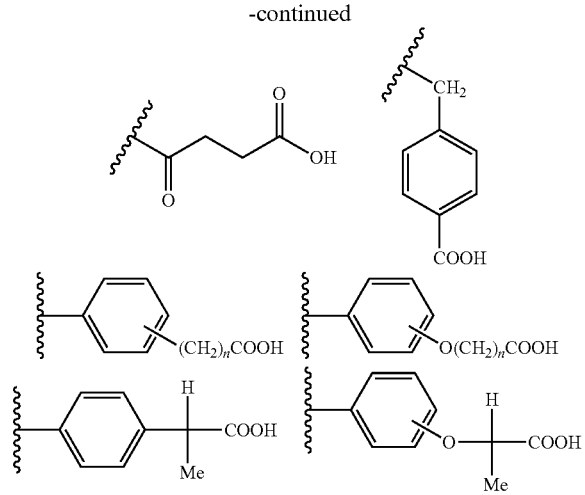

X is selected from the group consisting of hydrogen, —CO—, —CONHCHRCO—;

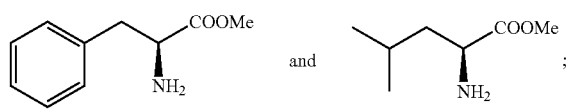

R is selected from the group consisting of hydrogen, alkyl, aryl, alkyl aryl, haloalkyl, alkoxy, hydroxy, halo, cyano, heteroaryl, alkyl heteroaryl, alkenyl, alkenyl aryl, alkenyl heteroaryl, alkynyl, alkynyl aryl, alkynyl heteroaryl, cycloalkyl, heterocycloalkyl, alkyl cycloalkyl, alkyl heterocycloalkyl, alkyl carboxy, acyl, alkyl acyl, alkyl acyloxy, alkyl alkoxy, alkoxycarbonyl, alkyl alkoxycarbonyl, aminocarbonyl, alkyl aminocarbonyl, alkyl acylamino, alkyl ureido, amino, alkyl amino, sulfonyloxy, alkyl sulfonyloxy, sulfonyl, alkyl sulfonyl, sulfinyl, alkyl sulfinyl, alkyl sulfanyl and alkyl sulfonylamino.

Y is selected from —PO (OR$_1$)$_2$ or —SO$_2$R wherein R$_1$ is selected from the group consisting of alkyl or aryl and alkyl aryl.

Provided, when Y=SO$_2$R, then L≠

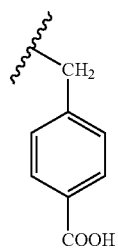

Another embodiment of the present invention provides process for the preparation of a new artemisinin-dipeptidyl vinyl based compounds of Formula (I) or a pharmaceutically acceptable salt thereof. The process comprises of coupling of dihydroartemisinin compound of Formula 12 with peptidyl-γ-amino vinyl phosphonate compounds through suitable linkers by using etherification reaction.

Yet another embodiment of the present invention provides a pharmaceutical composition comprising an artemisinin-dipeptidyl vinyl based compound of Formula (I), or a pharmaceutically acceptable salt thereof and a pharmaceutically acceptable carrier, diluent or excipient for treating malarial infection in a subject in need thereof by administering to said subject a therapeutically effective amount of the artemisinin-dipeptidyl vinyl based compound of Formula (I) or a pharmaceutically acceptable salt thereof.

BRIEF DESCRIPTION OF THE DRAWINGS

FIG. 1 shows effect of compounds 2, 3 and 5 on *P. falciparum* morphology.

DETAILED DESCRIPTION OF THE INVENTION

The invention will now be described in detail in connection with certain preferred and optional embodiments, so that various aspects thereof may be more fully understood and appreciated.

In view of the above, the present invention provides a new artemisinin-dipeptidyl vinyl based compounds of Formula (I) or a pharmaceutically acceptable salt thereof.

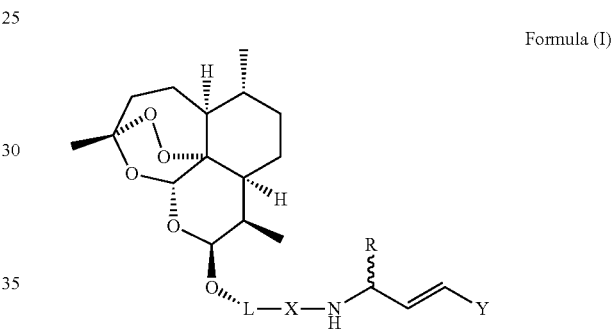

Formula (I)

Wherein, 'L' is Linker selected from group consisting of

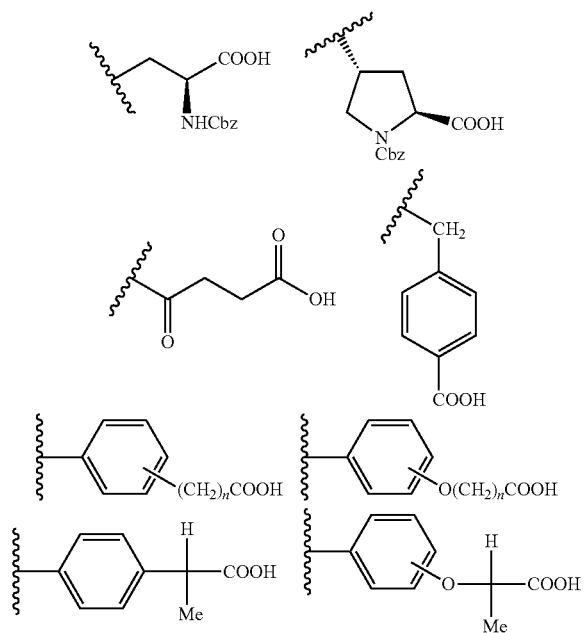

X is selected from the hydrogen, —CO—, —CONHCHRCO—;

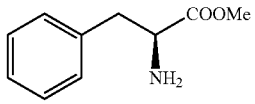 and 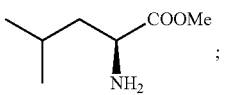 ;

R is selected from the group consisting of hydrogen, alkyl, aryl, alkyl aryl, haloalkyl, alkoxy, hydroxy, halo, cyano, heteroaryl, alkyl heteroaryl, alkenyl, alkenyl aryl, alkenyl heteroaryl, alkynyl, alkynyl aryl, alkynyl heteroaryl, cycloalkyl, heterocycloalkyl, alkyl cycloalkyl, alkyl heterocycloalkyl, alkyl carboxy, acyl, alkyl acyl, alkyl acyloxy, alkyl alkoxy, alkoxycarbonyl, alkyl alkoxycarbonyl, aminocarbonyl, alkyl aminocarbonyl, alkyl acylamino, alkyl ureido, amino, alkyl amino, sulfonyloxy, alkyl sulfonyloxy, sulfonyl, alkyl sulfonyl, sulfinyl, alkyl sulfinyl, alkyl sulfanyl and alkyl sulfonylamino.

Y is selected from —PO (OR$_1$)$_2$ or SO$_2$R wherein R$_1$ is selected from the group consisting of alkyl or aryl and alkyl aryl.

Provided, when Y=—SO$_2$R, then L≠

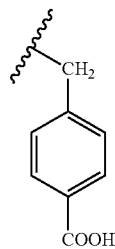

In a preferred embodiment, the artemisinin-dipeptidyl vinyl based compound of Formula (I) is selected from a group consisting of:

i) Benzyl ((2S)-1-(((E)-3-(diethoxyphosphoryl)-1-phenylallyl)amino)-1-oxo-3-(((3R,5aS,6R, 8aS,9R,10S,12R,12aR)-3,6,9-trimethyldecahydro-12H-3,12-epoxy[1,2]dioxepino[4,3-i]isochromen-10-yl)oxy)propan-2-yl)carbamate (1);

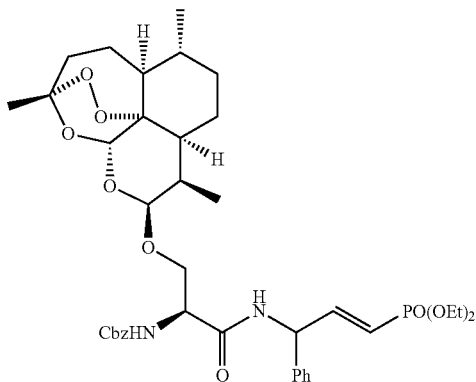

ii) Benzyl ((2S)-1-(((2S)-1-(((E)-3-(diethoxyphosphoryl)-1-phenylallyl)amino)-1-oxo-3-phenylpropan-2-yl)amino)-1-oxo-3-(((3R,5aS,6R,8aS,9R,10S,12R,12aR)-3,6,9-trimethyldeca hydro-12H-3,12-epoxy[1,2]dioxepino[4,3-i]isochromen-10-yl)oxy)propan-2-yl)carbamate (2);

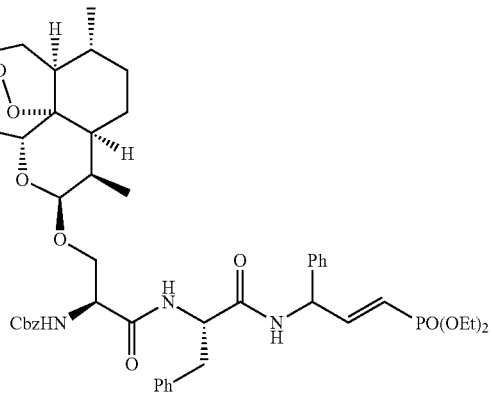

iii) Benzyl ((S)-1-(((S)-1-(((R,E)-3-(diethoxyphosphoryl)-1-phenylallyl)amino)-1-oxo-3-phenylpropan-2-yl)amino)-1-oxo-3-(((3R,5aS,6R,8aS,9R,10S,12R,12aR)-3,6,9-trimethyldeca hydro-12H-3,12-epoxy[1,2]dioxepino[4,3-i]isochromen-10-yl)oxy)propan-2-yl)carbamate (2a);

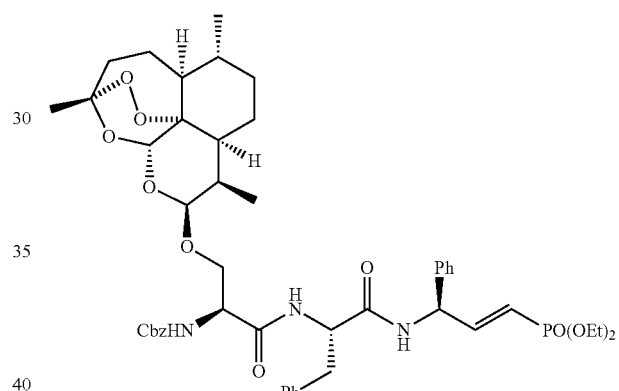

iv) Benzyl ((S)-1-(((S)-1-(((S,E)-3-(diethoxyphosphoryl)-1-phenylallyl)amino)-1-oxo-3-phenylpropan-2-yl)amino)-1-oxo-3-(((3R,5aS,6R,8aS,9R,10S,12R,12aR)-3,6,9-trimethyldeca hydro-12H-3,12-epoxy[1,2]dioxepino[4,3-i]isochromen-10-yl)oxy)propan-2-yl)carbamate (2b);

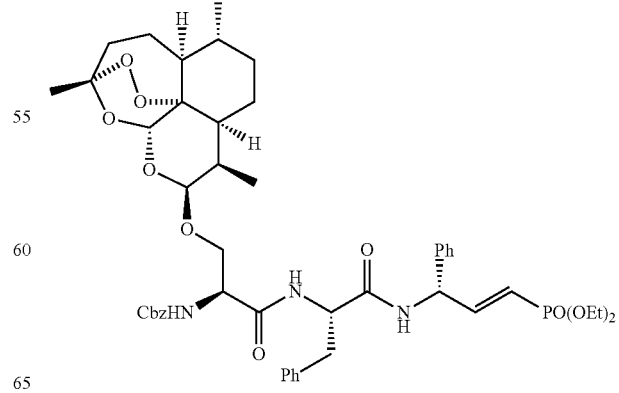

v) Benzyl ((2S)-1-(((2S)-1-(((E)-3-(diethoxyphosphoryl)-1-phenylallyl)amino)-4-methyl-1-oxopentan-2-yl)amino)-1-oxo-3-(((3R,5aS,6R,8aS,9R,10S,12R,12aR)-3,6,9-trimethyldecahydro-12H-3,12-epoxy[1,2]dioxepino[4,3-i]isochromen-10-yl)oxy)propan-2-yl)carbamate (3);

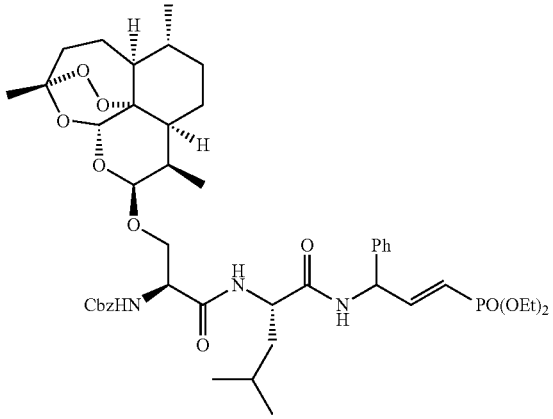

vi) Benzyl ((S)-1-(((S)-1-(((R,E)-3-(diethoxyphosphoryl)-1-phenylallyl)amino)-4-methyl-1-oxopentan-2-yl)amino)-1-oxo-3-(((3R,5aS,6R,8aS,9R,10S,12R,12aR)-3,6,9-trimethyldecahydro-12H-3,12-epoxy[1,2]dioxepino[4,3-i]isochromen-10-yl)oxy)propan-2-yl)carbamate (3a);

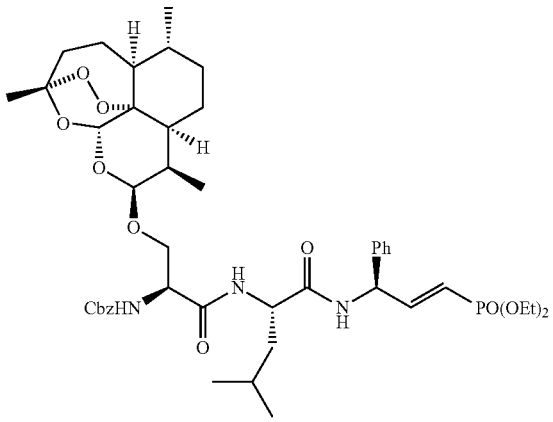

vii) Benzyl ((S)-1-(((S)-1-(((S,E)-3-(diethoxyphosphoryl)-1-phenylallyl)amino)-4-methyl-1-oxopentan-2-yl)amino)-1-oxo-3-(((3R,5aS,6R,8aS,9R,10S,12R,12aR)-3,6,9-trimethyldecahydro-12H-3,12-epoxy[1,2]dioxepino[4,3-i]isochromen-10-yl)oxy)propan-2-yl)carbamate (3b);

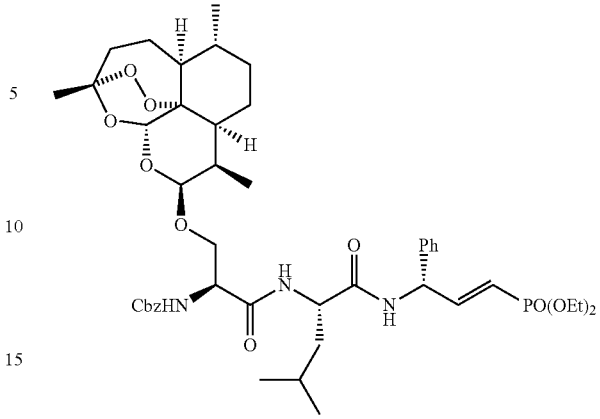

viii) Benzyl (2S,4R)-2-(((E)-3-(diethoxyphosphoryl)-1-phenylallyl)carbamoyl)-4-(((3R,5aS, 6R,8aS,9R,10S,12R,12aR)-3,6,9-trimethyldecahydro-12H-3,12-epoxy[1,2]dioxepino[4,3-i]isochromen-10-yl)oxy)pyrrolidine-1-carboxylate (4);

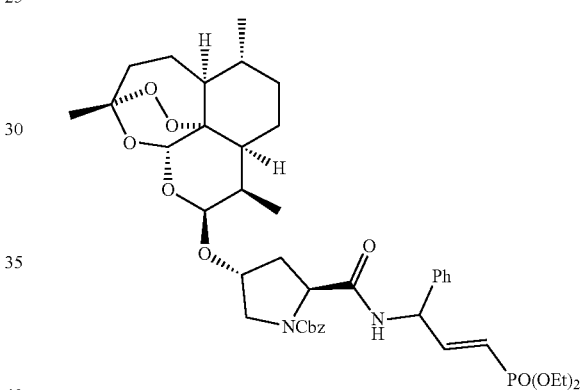

ix) Benzyl (2S,4R)-2-(((2S)-1-(((E)-3-(diethoxyphosphoryl)-1-phenylallyl)amino)-4-methyl-1-oxopentan-2-yl)carbamoyl)-4-(((3R,5aS,6R,8aS,9R,10S,12R,12aR)-3,6,9-trimethyldecahydro-12H-3,12-epoxy[1,2]dioxepino[4,3-i]isochromen-10-yl)oxy)pyrrolidine-1-carboxylate (5);

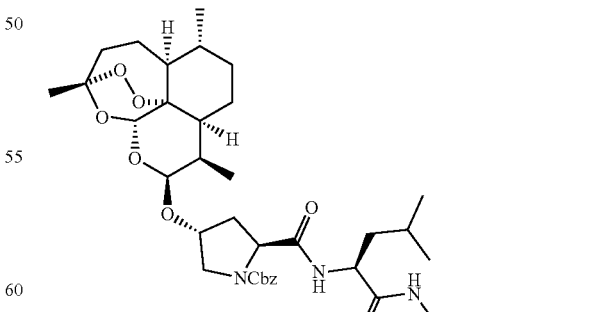

x) Benzyl (2S,4R)-2-(((S)-1-(((R,E)-3-(diethoxyphosphoryl)-1-phenylallyl)amino)-4-methyl-1-oxopentan-2-yl)carbamoyl)-4-(((3R,5aS,6R,8aS,9R,10S,12R,12aR)-3, 6,9-trimethyldeca hydro-12H-3,12-epoxy[1,2] dioxepino[4,3-i]isochromen-10-yl)oxy)pyrrolidine-1-carboxylate (5a);

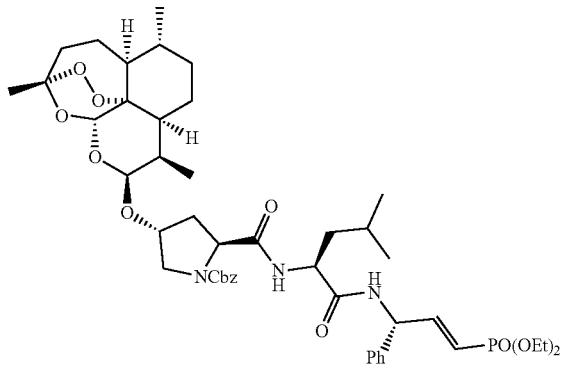

xi) Benzyl (2S,4R)-2-(((S)-1-(((S,E)-3 -(diethoxyphosphoryl)-1-phenylallyl)amino)-4-methyl-1-oxopentan-2-yl)carbamoyl)-4-(((3R,5aS,6R,8aS,9R,10S,12R,12aR)-3,6,9-trimethyldeca hydro-12H-3,12-epoxy[1,2] dioxepino[4,3-i]isochromen-10-yl)oxy)pyrrolidine-1-carboxylate (5b);

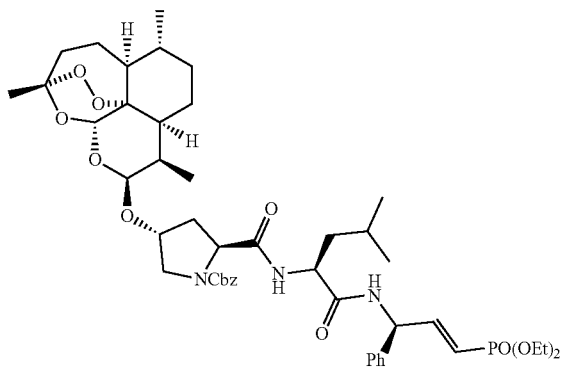

xii) Benzyl (2S,4R)-2-(((2S)-1-(((E)-3-(diethoxyphosphoryl)-1-phenylallyl)amino)-1-oxo-3 -phenylpropan-2-yl)carbamoyl)-4-(((3R,5aS,6R,8aS,9R,10S,12R,12aR)-3,6,9-trimethyl decahydro-12H-3,12-epoxy[1,2] dioxepino[4,3-i]isochromen-10-yl)oxy)pyrrolidine-1-carboxylate (6).

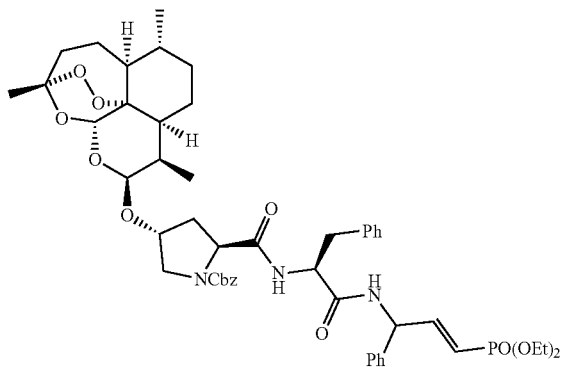

Yet another embodiment of the present invention provides process for the preparation of a new artemisinin-dipeptidyl based compound of Formula (I) or a pharmaceutically acceptable sat thereof, wherein said process comprises of coupling of dihydroartemisinin compound of Formula 12 with peptidyl-γ-amino vinyl phosphonate compounds through suitable linkers by using etherification reaction.

The process for the synthesis of artemisinin-dipeptidyl vinyl based compound of Formula (I) is represented in scheme 1 herein below;

Scheme 1

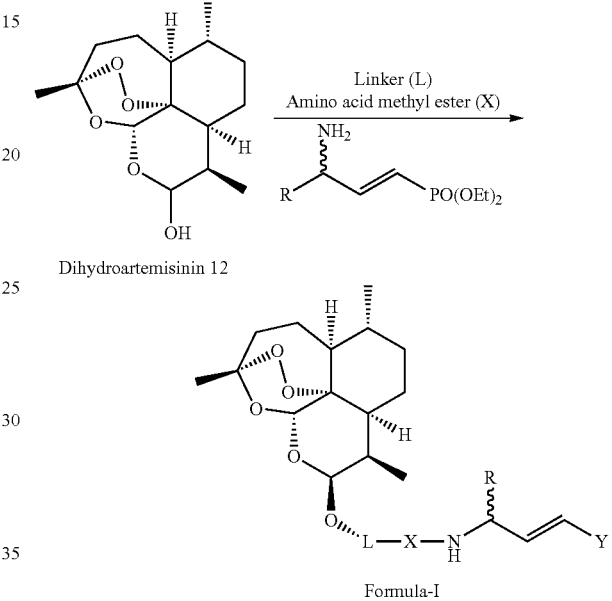

The process for the synthesis of novel artemisinin-dipeptidyl vinyl based compound of Formula (I) comprising the steps of:
a) adding Lewis acid to a solution of compound of Formula 12 in a suitable solvent and linker 'L' in a suitable solvent at temperature in the range of 25to 30° C. for the period in the range of 2 to 6 hr to afford linker attached artemisinin compounds;
b) hydrolyzing the ester of linker attached artemisinin compounds obtained from step a) to free acid by adding aqueous solution of alkaline hydrolyzing agent in suitable solvent at temperature in the range of 25 to 30° C. with constant stirring to afford the corresponding artemisinin free acid compound;
c) subjecting the free acid compound obtained from step (b) to peptide coupling reaction with alkyl ester of phenylalanine or alkyl ester of leucine in the presence of coupling reagent N,N'-Dicyclohexylcarbodiimide (DCC) and Hydroxybenzotriazole (HOBt) in suitable solvent at suitable temperature to afford corresponding dipeptide;
d) subjecting the free acid compound obtained from step (b) or dipeptide of step (c) to peptide coupling reaction with γ-amino vinyl phosphonate compounds in the presence of coupling regents N,N'-Dicyclohexylcarbodiimide (DCC) and Hydroxybenzotriazole (HOBt) in a suitable solvent at suitable temperature to afford artemisinin-dipeptidyl vinyl based compound of Formula (I).

Lewis acid is selected from the group consisting of Boron trifluoride diethyl etherate ($BF_3.Et_2O$), Silicon tetrabromide ($SiBr_4$), Silicon tetrafluoride ($SiF_4$) or Aluminium fluoride ($AlF_3$). In particularly preferred embodiment, boron trifluoride etherate is used at step a).

Solvent used at step a) may include the polar solvents, non-polar solvents, alcohol solvents, ether solvents, ester solvents, amide solvents and the mixtures thereof. Polar solvents may include water, ammonia, sulfuric acid, deuterium oxide, ethanol, methanol, acetone, isopropanol, methyl ethyl ketone, n-propanol, acetonitrile, DMSO, and DMF and mixtures thereof. Nonpolar solvents may include chloroform, pentane, hexane, benzene, toluene, octane, decane, dimethyl ether, and dichloromethane, and mixtures thereof. Alcohol solvents may include methanol, ethanol, isopropanol, and mixtures thereof. Ether solvents may include tetrahydrofuran, diethyl ether, 1,4-dioxane, methyl tert-butyl ether, and mixtures thereof. Ester solvents may include methyl acetate, ethyl acetate, isopropyl acetate, tert-butyl acetate, and mixtures thereof. In particularly useful embodiments, non-polar solvents are used and most preferably dichloromethane is used as a solvent in step a).

Suitable temperature to conduct the reaction at step a) is in the range of 0° C.-35° C. In particularly useful embodiment, reaction at step a) is conducted at 27° C.

The alkaline hydrolyzing agent used at step b) for ester hydrolysis is selected from the group comprising of Lithium hydroxide (LiOH), Sodium hydroxide (NaOH), Potassium hydroxide (KOH), Calcium hydroxide [$Ca(OH)_2$], Barium hydroxide [$Ba(OH)_2$], Magnesium hydroxide [$Mg(OH)_2$] either alone or in combination thereof. In particularly useful embodiment, lithium hydroxide (LiOH) is used at step b).

Solvent used at step b) may include the polar solvents, non-polar solvents, alcohol solvents, ether solvents, ester solvents, amide solvents and the mixtures thereof. Polar solvents may include water, ammonia, sulfuric acid, deuterium oxide, ethanol, methanol, acetone, isopropanol, methyl ethyl ketone, n-propanol, acetonitrile, DMSO, and DMF and mixtures thereof. Nonpolar solvents may include chloroform, pentane, hexane, benzene, toluene, octane, decane, dimethyl ether, and dichloromethane, and mixtures thereof. Alcohol solvents may include methanol, ethanol, isopropanol, and mixtures thereof. Ether solvents may include tetrahydrofuran, diethyl ether, 1,4-dioxane, methyl tert-butyl ether, and mixtures thereof. Ester solvents may include methyl acetate, ethyl acetate, isopropyl acetate, tert-butyl acetate, and mixtures thereof. In particularly useful embodiments, ether solvents are used and most preferably tetrahydrofuran is used as a solvent in step b).

Suitable temperature to conduct the reaction at step b) is in the range of 0° C.-35° C. In particularly useful embodiment, reaction at step b) is conducted at 27° C.

Solvent used at step c) and d) may include the polar solvents, non-polar solvents, alcohol solvents, ether solvents, ester solvents, amide solvents and the mixtures thereof. Polar solvents may include water, ammonia, sulfuric acid, deuterium oxide, ethanol, methanol, acetone, isopropanol, methyl ethyl ketone, n-propanol, acetonitrile, DMSO, and DMF and mixtures thereof. Nonpolar solvents may include chloroform, pentane, hexane, benzene, toluene, octane, decane, dimethyl ether, and dichloromethane, and mixtures thereof. Alcohol solvents may include methanol, ethanol, isopropanol, and mixtures thereof. Ether solvents may include tetrahydrofuran, diethyl ether, 1,4-dioxane, methyl tert-butyl ether, and mixtures thereof. Ester solvents may include methyl acetate, ethyl acetate, isopropyl acetate, tert-butyl acetate, and mixtures thereof. In particularly useful embodiments, ether solvents are used and most preferably tetrahydrofuran is used as a solvent in step c) and d).

Suitable temperature to conduct the reaction at step c) and d) is the range of 0° C.-35° C.

The alkyl ester of phenylalanine is selected from methyl ester of phenylalanine ($NH_2$-Phe-OMe) or ethyl ester of phenylalanine ($NH_2$-Phe-OEt) and the alkyl ester of leucine is selected from methyl ester of leucine ($NH_2$-Leu-OMe) or ethyl ester of leucine ($NH_2$-Leu-OEt).

Yet another embodiment of the present invention provides a pharmaceutical composition comprising a compound of Formula (I), or a pharmaceutically acceptable salt thereof, and a pharmaceutically acceptable carrier, diluent or excipient.

Still another embodiment of the present invention provides a pharmaceutical composition comprising a compound of Formula (I) or its pharmaceutically acceptable salts, along with pharmaceutically acceptable excipients or carriers, for the treatment against growth of malarial parasite (*Plasmodium falciparum*).

The pharmaceutical compositions of the invention can be prepared by combining a compound of Formula (I) with an appropriate pharmaceutically acceptable carrier, diluent or excipient known in the art. The excipients or carriers are selected from the group such as diluents, disintegrates, crosslinked polymers, binders, lubricants, coatings layer.

In another embodiment, the present invention relates to administering 'an effective amount' of the 'composition of invention' to the subject suffering from malaria. Accordingly, compound of Formula (I) and pharmaceutical compositions containing compound of Formula (I) may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Generally, the quantity of active compound ranges between 0.5% to 90% by weight of the composition. Normally, the effective amount of dosage of falcipain-2 inhibitor component ranges about 0.1 to about 100 mg/kg, more preferably about 1.0 mg to about 50 mg/kg of body weight/day.

The pharmaceutical compositions may be administered to a subject or patient may take the form of one or more dosage units. The dosage forms may also be prepared as sustained, controlled, modified and immediate dosage forms.

The pharmaceutical compositions of the invention may be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres.

Pharmaceutical compositions of the invention may be formulated so as to allow the active ingredients contained therein to be bioavailable upon administration of the composition to a patient. Compositions that may be administered to a subject or patient may take the form of one or more dosage units. The dosage forms can also be prepared as sustained, controlled, modified and immediate dosage forms.

In one embodiment, the invention provides a method of inhibiting cysteine protease and growth of *P. falciparum* in a subject comprising administrating cysteine protease falcipain-2 inhibitor artemisinin-dipeptidyl vinyl based compound of Formula (I) optionally comprising administering at least one additional active compound together with pharmaceutically acceptable excipients and/or vehicles.

In another embodiment, the present invention provides the use of artemisinin-dipeptidyl vinyl based compound of Formula (I) for the preparation of medicament useful for inhibiting cysteine protease and growth of *P. falciparum* in a subject, wherein the subject is mammal.

In yet another embodiment, the present invention provides use of artemisinin-dipeptidyl vinyl based compound of Formula (I) as cysteine protease inhibitor for treating malarial infection.

In still another embodiment, the present invention provides use of artemisinin-dipeptidyl vinyl based compound of Formula (I) as antimalarial agent or anticancer agent or anti-HIV agent.

In preferred embodiment, the present invention provides a method for the treating malarial infection in a subject in need thereof; comprising administering to the said subject a therapeutically effective amount of the compound of Formula (I) or a pharmaceutically acceptable salt thereof.

The artemisinin-dipeptidyl vinyl based compound of Formula (I) exhibits very effective parasiticidal effect in vitro and in vivo; the parasicitidal efficacies are higher than the existing antimalarial agents. The parasite is preferably malarial parasite (*Plasmodium falciparum*).

The instant dual-targeting artemisinin-dipeptidyl vinyl based compound of Formula (I) with more than 7 fold are potential candidates against parasite as compared to artemisinin alone. These compounds are able to inhibit in vitro *Plasmodium falciparum* parasite at $IC_{50}$ which is ~7.5 less than that of artemisinin. In addition, the compounds effectively killed *P. falciparum* strains that are resistance to commonly used antimalarial compounds such as Chloroquine, Pyremethmine and Mefloquine.

The synthesized artemisinin-dipeptidyl vinyl based compound of Formula (I) have excellent in vivo antimalarial efficacies. Results show that the treatment with these compounds (12.5 mg/kg of body weight) completely cleared the parasites in infected mice and 100% protection is shown in treated group of mice as compared to untreated control where all mice died after 10-15 days of infection. Therefore the $ED_{99}$ in mice is lower than those of the reference antimalarial drugs chloroquine, artesunate, and mefloquine.

All the synthesized artemisinin-dipeptidyl vinyl based compounds of Fomrula (I) are assayed for their inhibition activity against falcipain-2 protease enzyme. The inhibitions of falcipain-2 enzyme by all the hybrid molecules are expressed in $IC_{50}$ values and are summarized in Table 1.

Among all six synthesized hybrid molecules, dipeptide hybrid compounds of Formulae 2, 3 and 5 exhibited falcipain-2 enzyme inhibition in μM range whereas mono peptide hybrid compounds of Formulae 1 and 4 are found to be inactive against falcpain-2 enzyme. The dipeptide hybrid compound of Formula 2 having phenylalanine residue in P2 pocket and serine in $P_3$ pocket shows $IC_{50}$ value of 5.90 μM against FP-2 enzyme. The dipeptide hybrid compound of Formula 3 having leucine residue in $P_2$ pocket and serine in $P_3$ pocket shows $IC_{50}$ value of 5.62 μM against FP-2. The dipeptide hybrid compound of Formula 5 having leucine residue in $P_2$ pocket and hydroxyproline in $P_3$ pocket shows $IC_{50}$ value of 5.62 μM against FP-2 whereas the dipeptide hybrid compound of Formula 6 having phenylalanine residue in $P_2$ pocket and hydroxyproline in $P_3$ pocket is found to be inactive against FP-2. The inactivity of mono peptide hybrid compounds of Formulae 1 and 4 against FP-2 may be attributed due to the complete absence of $P_2$ pocket residue.

TABLE 1

Inhibition of falcipain-2 activity by compounds.

| Compound | $IC_{50}$ (μM) | $K_i$ (μM) |
|---|---|---|
| 1 | >100 | NA |
| 2 | 5.90 ± 0.45 | 3.49 ± 0.2668 |
| 3 | 5.62 ± 0.30 | 3.32 ± 0.177 |
| 4 | >100 | NA |
| 5 | 7.67 ± 0.35 | 4.54 ± 0.206 |
| 6 | >100 | NA |

Further, all the synthesized artemisinin-peptidyl vinyl based compounds of Formula (I) are assayed for their antiplasmodial activities against different strains such as chloroquine-sensitive (3D7), chloroquine-pyrimethamine resistant (7G8) and chloroquine-pyrimethamine-mefloquine resistant (Dd2) strains of *P. falciparum* (Table 2). Among these, compounds of Formulae 2, 3 and 5 are found to exhibit very effective parasiticidal activities in vitro and in vivo. The parasiticidal efficacies of the compounds of Formulae 2, 3 and 5 are higher than the existing antimalarial agent, artemisinin.

The instant dual-targeting artemisinin-dipeptidyl vinyl based compounds of Formulae 2, 3 and 5 are found to be several-fold more potent than artemisinin alone against various strains of parasites. Also, the hybrid molecules effectively killed *P. falciparum* strains that are resistant to commonly used antimalarial compounds such as chloroquine, pyrimethamine and mefloquine. The results are summarized in Table 2.

The antiplasmodial activity data in Table 2 suggests that the compounds of Formulae 2, 3 and 5 exhibits potent antiplasmodial activities in the nM range against all the strains of *P. falciparum*, being more active than artemisinin. The compound of Formula 2 displays $EC_{50}$ values of 2.7, 0.47 and 1.9 nM against 3D7, 7G8 and Dd2 strains of *P. falciparum*, respectively. The compound of Formula 3 shows $EC_{50}$ values of 3.3, 0.23 and 3.5 nM against 3D7, 7G8 and Dd2 strains of *P. falciparum*, respectively. The compound of Fomrula 5 shows $EC_{50}$ values of 2.57, 1.2 and 5.5 nM against 3D7, 7G8 and Dd2 strains of *P. falciparum*, respectively.

TABLE 2

Parasiticidal activity of selected compounds on *P. falciparum* in vitro culture.

| Compound | $EC_{50}$ on *P. falciparum* 3D7(nM) | $EC_{50}$ on *P. falciparum* 7G8*(nM) | $EC_{50}$ on *P. falciparum* Dd2**(nM) |
|---|---|---|---|
| 2 | 2.7 | 0.47 | 1.9 |
| 3 | 3.3 | 0.23 | 3.5 |
| 5 | 2.57 | 1.2 | 5.5 |
| Artemisinin | ~27 | ~18 | ~15 |

*Chloroquine and Pyrimethamine resistant
**Chloroquine, Pyrimethamine and Mefloquine resistant The artemisinin-dipeptidyl vinyl based compound of Formulae 2, 3 and 5 show excellent in vivo antimalarial efficacies as summarized in Table 3. Results show that the treatment with these compounds (12.5 mg/kg of body weight) completely cleared the parasites in infected mice and 100% protection is shown in treated group of mice as compared to untreated control where all mice died after 10-15 days of infection. Moreover, the survival days of mice after treatment with the compounds of Formulae 2, 3 and 5 are found to be >60 days.

TABLE 3

Protection of mice against malaria after treatment with selected compounds.

| Compound (4 doses of 12.5 mg/Kg of body weight) | Complete Protection - Mice with complete parasite clearance (% of treated mice) | Survival after treatment (Days) |
| --- | --- | --- |
| 2 | 80% | >60 |
| 3 | 100% | >60 |
| 5 | 100% | >60 |
| Artemisinin | 0% | 15-25 |
| Control (solvent alone) | 0% | 12-15 |

The compounds of Formulae 2, 3 and 5 are further assayed for their in vitro toxicity on mammalian cell culture (A549 human cells) and are found to be non-toxic to the human cells. The $EC_{50}$ values of these compounds on A549 human cells are shown in Table 4.

TABLE 4

In vitro toxicity of selected compounds on mammalian cell culture.

| Compound | $EC_{50}$ on A549 human cells (nM) |
| --- | --- |
| 2 | 14600 ± 174.8 |
| 3 | 3816 ± 160.6 |
| 5 | 1282 ± 156.1 |

FIG. 1 shows the effect of selected compounds of Formulae 2, 3 and 5 on the morphology and development of *P. falciparum* through its asexual stage. The ring stage parasites are treated with the selected compounds or solvent alone as control.

Antimalarial Activity of Diastereomers of Artemisinin-Dipeptidyl vinyl based compounds of Fomrulae 2, 3 and 5 (2a & 2b, 3a & 3b and 5a & 5b):

All the synthesized diastereomers of hybrid molecules 2, 3 and 5 (i.e., 2a & 2b, 3a & 3b and 5a & 5b) are assayed for their efficacy against falcipain-2 enzyme. The inhibition of falcipain-2 activity of all the synthesized diastereomers are summarized in Table 5.

It is evident from the Table 5 that the diastereomer 2a synthesized from (R)-γ-phenyl-γ-amino vinyl phosphonate (R)-22 is found to be more active against FP-2 than the corresponding diastereomer 2b synthesized from (S)-γ-phenyl-γ-amino vinyl phosphonate (S)-22. Similarly, diastereomers 3a and 5a are found to show more FP-2 inhibition activities than the corresponding diastereomers 3b and 5b, respectively.

TABLE 5

Inhibition of falcipain-2 activity by compounds.

| Compound | $IC_{50}$ (µM) | $K_i$ (µM) |
| --- | --- | --- |
| 3a | 3.78 ± 0.52 | 2.78 |
| 3b | 13.46 ± 6.74 | 9.92 |
| 3a | 3.38 ± 0.47 | 2.49 |
| 3b | 9.38 ± 1.97 | 6.91 |
| 5a | 3.53 ± 0.25 | 2.60 |
| 5b | >10 | NA |

Further, all the diastereomers 2a & 2b, 3a & 3b and 5a & 5b are assayed for their antiplasmodial activities against 3D7 strain of *P. falciparum* as shown in Table 6. All the diastereomers show potent antiplasmodial activities in nM range compared to the existing antimalarial agent, artemisinin.

Also, the diastereomers 2a, 3a and 5a are found to be more active than the corresponding diastereomers 2b, 3b and 5b. The in vitro antiplasmodial activities of all the diastereomers on 3D7 strain of *P. falciparum* are summarized in Table 6.

The diastereomer 2a exhibits $EC_{50}$ value of 0.95 nM against the 3D7 strain of *P. falciparum* whereas 2b exhibits $EC_{50}$ value of 2.03 nM against the 3D7 strain of *P. falciparum*. The diastereomer 3a shows $EC_{50}$ value of 10.90 nM against the 3D7 strain whereas 3b shows $EC_{50}$ value of 16.73 nM against the 3D7 strain. Similarly, the diastereomer 5a exhibits $EC_{50}$ value of 1.04 nM against the 3D7 strain whereas 5b exhibits $EC_{50}$ value of 6.12 nM against the 3D7 strain.

TABLE 6

Parasiticidal activity of selected compounds on *P. falciparum* in vitro culture.

| Compound | $EC_{50}$ on *P. falciparum* 3D7 nM(SD) |
| --- | --- |
| 2a | 0.95 ± 0.49 |
| 2b | 2.03 ± 3.10 |
| 3a | 10.90 ± 39.6 |
| 3b | 16.73 ± 12.40 |
| 5a | 1.04 ± 0.53 |
| 5b | 6.12 ± 23.58 |
| Artemisinin | ~27 |

In conclusion, the dual-targeting compounds of Formulae 2a and 5a may be considered as the ideal compounds for the further development of novel antimalarial drugs with a different mode of action.

EXAMPLES

Following examples are given by way of illustration therefore should not be construed to limit the scope of the invention.

All the *Plasmodium falciparum* strains used in present study (3D7, 7G8 and Dd2) were obtained from -Malaria Research and Reference Reagent Resource Center (MR4). The linkers 8 and 10 are synthesized from their corresponding free amino acids by following the literature procedure (*Org. Biomol. Chem.* 2015, 13, 7177 and *J. Am. Chem. Soc.* 2001, 123, 10245)

Example 1:

Compound 12 was prepared by following the reported literature procedure (*Asian J. Org. Chem.* 2016, 5(2), 201-206).

Example 2: General Procedure for Hydrolysis of Methyl Ester to Corresponding Free Acid Methyl ester (13 or 14 or 15 or 16 or 17 or 18) (1.5 mmol) was dissolved in THF (17 mL) and a solution of 2M aq. LiOH (7 mL) was added to it at 25° C. with stirring. After completion of the reaction (TLC after 2 h), THF was evaporated and the remaining aqueous layer was neutralized with acetic acid. The compound was extracted with ethyl acetate (3×20 mL), dried over $Na_2SO_4$ and concentrated under vacuum to obtain the crude product, which was purified by silica gel column chromatography with ethyl acetate: petroleum ether (3:2 to 4:1) as eluant.

Example 3: General Procedure for the Synthesis of Diethyl (E)-(3-amino-3-phenylprop-1-en-1-yl)phosphonate (22)

a) General Procedure for the Synthesis of 2-phenyl-2-(tritylamino)ethan-1-ol (19):

To a mixture of phenylglycinol (±)-19 or (R)-19 or (S)-19 (1.0 g, 1.0 eq) and triphenylmethyl chloride (2.03 g, 1.0 eq) in dichloromethane (25 mL) was added triethylamine (0.74 g, 1.0 eq). The resulting mixture was stirred at 25° C. for 12 h. The mixture was diluted with ethyl acetate (75 mL) and washed with water and brine. The ethyl acetate fraction was dried (MgSO$_4$), filtered and concentrated. The solid was purified by chromatography on a silica gel column with ethyl acetate: petroleum ether as eluent to furnish the pure product as colorless foaming solid.

b) General Procedure for the Synthesis of Diethyl (E)-(3-phenyl-3-(tritylamino)prop-1-en-1-yl)phosphonate (21)

2-phenyl-2-(tritylamino) ethan-1-ol (±)-19 or (R)-19 or (S)-19 (1.32 mmol, 1.0 eq) was dissolved in DCM (10 mL) and cooled to 0° C. To this cold solution was added Dess-Martin periodinane (1.98 mmol, 1.5 eq) portion wise over 10 min and then stirred at 0° C. for 10 min. The reaction mixture was allowed to slowly warm to 25° C. and stirred for 30 min. After completion of the reaction (TLC), the reaction mixture was diluted with DCM. The reaction mixture was placed in an ice-water bath and a 1:1 mixture of saturated aqueous NaHCO$_3$ solution and saturated NaHSO$_3$ solution (4 mL) was added and the cooling bath was removed and the mixture was stirred at 25° C. until the formation of two clear layers was observed. The reaction mixture was transferred to a separatory funnel containing saturated aqueous NaHCO$_3$ solution (20 mL). The aqueous layer was extracted with ethyl acetate (3×25 mL). The combined organic layers were washed with brine (20 mL), dried over MgSO$_4$, filtered and concentrated to give crude aldehyde (±)-20 or (R)-20 or (S)-20 as colorless foaming solid. The residue (±)-20 or (R)-20 or (S)-20 was used for the next step without any further purification.

Tetraethyl methylenediphosphonate (2.24 mmol, 1.7 eq) was taken up in dry THF (4 mL) and was cooled to 0° C. in an ice bath. NaH (60% dispersion in mineral oil, 1.98 mmol, 1.5 eq) was added to the reaction mixture in portion wise over a period of 5-10 min. The solution was stirred at 0° C. for 15 min. Crude aldehyde (±)-20 or (R)-20 or (S)-20 was taken in dry THF (4 mL) and was added to the reaction mixture. The reaction mixture was then warmed to 25° C. and stirred for 3 h. After completion of the reaction (TLC), reaction mixture was diluted with DCM and concentrated in vacuo. The residue was dissolved in water, extracted with DCM (3×20 mL). The combined organic layers were washed with water, brine and concentrated to give crude product which was purified either by recrystallization from EtOAc-Petroleum ether mixture or column chromatography on a silica gel column with ethyl acetate: petroleum ether as eluant to give colorless solid; $^1$H NMR (500 MHz, CDCl$_3$) δ: 7.51-7.41 (m, 6H), 7.24-7.18 (m, 6H), 7.18-7.10 (m, 6H), 6.99-6.92 (m, 2H), 6.56-6.44 (m, 1H), 5.73-5.62 (m, 1H), 4.31-4.25 (m, 1H), 4.03-3.87 (m, 4H), 1.32-1.21 (m, 6H); $^{13}$C NMR (125 MHz, CDCl$_3$) δ: 155.5, 155.4, 146.1, 142.3, 128.9, 128.4, 127.8, 127.0, 126.8, 126.6, 115.7, 114.2, 71.9, 61.7, 61.6, 61.6, 61.6, 60.5, 60.3, 16.4, 16.4, 16.3, 16.3.

c) General Procedure for the Synthesis of Diethyl (E)-(3-amino-3-phenylprop-1-en-1-yl)phosphonate (22):

Trityl protected amine (±)-21 or (R)-21 or (S)-21 (0.5 g, 1.0 eq) was dissolved in DCM (5 mL) and Trifluoroacetic acid (150 µL, 3.0 eq) was added at 25° C. and reaction mixture was stirred for 30 min. After completion of the reaction (TLC), DCM was removed under reduced pressure. Water (10 mL) was added to the residue and the aqueous layer was washed with diethyl ether (3×20 mL). The remaining aqueous layer was basified with saturated aqueous solution of NaHCO$_3$ until pH 9, after which it was extracted with DCM (3×20 mL). The combined organic layers were dried over Na$_2$SO$_4$ and concentrated to give crude amine as pale yellow/colorless syrup in quantitative yield, which was used for the final coupling reaction without any further purification. $^1$H NMR (200 MHz, CDCl$_3$): δ 7.51-7.16 (m, 5H), 7.08-6.76 (m, 1H), 6.10-5.83 (m, 1H), 4.74-4.59 (m, 1H), 4.21-3.93 (m, 4H), 1.43-1.18 (m, 6H); $^{13}$C NMR (50 MHz, CDCl$_3$): δ 155.0, 154.9, 142.3, 128.8, 127.7, 127.5, 126.8, 125.9, 117.4, 113.7, 61.8, 61.7, 58.3, 57.8, 16.4, 16.3; ESI-LCMS: m/z 292.0 [M+Na]$^+$.

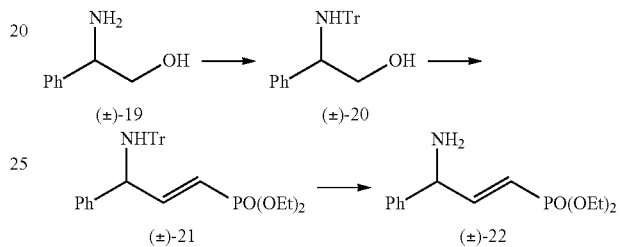

Example 4: General Procedure for Peptide Coupling Reaction

γ-amino vinyl phosphonate (±)-22 or (R)-22 or (S)-22 (0.5 mmol), HOBt (0.5 mmol) and free acid obtained from the ester hydrolysis of 13 or 14 or 15 or 16 or 17 or 18 (0.5 mmol) were dissolved in dry THF (5 mL) and the resulting solution was stirred in an ice-cooled water bath then DCC (0.6 mmol) was added. Stirring was continued for 1 h at 0° C. and then an additional 1 h at 25° C. The solid which precipitated was removed by filtration and the solvent evaporated in vacuum. After evaporation of the solvent, the resulting crude product was dissolved in EtOAc and washed with saturated aqueous NaHCO$_3$ solution (3×20 mL). Finally, the crude peptide derivative was purified by chromatography on a silica gel column to furnish the corresponding peptide.

Example 5: Methyl N-((benzyloxy)carbonyl)-O-((3R,5aS,6R,8aS,9R,10S,12R,12aR)-3,6,9-trimethyl decahydro-12H-3,12-epoxy[1,2]dioxepino[4,3-i]isochromen-10-yl)-L-serinate (13)

To a solution of dihydroartemisinin 12 (5.7 g, 20 mmol) and alcohol 8 (6.07 g, 24 mmol) in DCM (80 mL), BF$_3$.Et$_2$O (0.5 mL) was added. The resulting mixture was stirred at 25° C. for 3 hr and then washed with aqueous NaHCO$_3$ (20 mL) followed by brine (20 mL). The organic layers were dried over (Na$_2$SO$_4$) and concentrated in vacuum to afford the crude product which was purified by column chromatography (silica gel) using ethyl acetate: petroleum ether (1:9) as eluant to furnish the pure product 13 (7.3 g, 71%) as colourless syrup; [α]$^{20}_D$=+57.76 (c 1.0, CHCl$_3$); IR (CHCl$_3$): 3439, 3019, 2955, 2876, 1723, 1698, 1505, 1455, 1377, 1215, 1028 cm$^{-1}$; $^1$H NMR (200 MHz, CDCl$_3$): δ 0.82 (d, J=7.3 Hz, 3H), 0.92 (d, J=5.7 Hz, 3H), 1.13-1.33 (m, 3H), 1.41 (s, 3H), 1.46-1.74 (m, 5H), 1.81-1.89 (m, 1H), 1.91-

2.07 (m, 1H), 2.28-2.43 (m, 1H), 2.57-2.65 (m, 1H), 3.74 (s, 3H), 3.87-4.10 (m, 2H), 4.52-4.60 (m, 1H), 4.74 (d, J=3.5 Hz, 1H), 5.13 (s, 2H), 5.37 (s, 1H), 5.74 (d, J=8.6 Hz, NH), 7.34-7.39 (s, 5H); (ESI): m/z 542.8 (M+Na)$^+$; HRMS (ESI) m/z for $C_{27}H_{37}NO_9$ [M+Na]$^+$ calcd 542.2360, found: 542.2361.

Example 6: 1-benzyl 2-methyl (2S,4R)-4-(((3R,5aS, 6R,8aS,9R,10S,12R,12aR)-3,6,9-trimethyldeca hydro-12H-3,12-epoxy[1,2]dioxepino[4,3-i]iso-chromen-10-yl)oxy)pyrrolidine-1,2-dicarboxylate (14)

To a solution of dihydroartemisinin 12 (5.7 g, 20 mmol) and alcohol 10 (6.7 g, 24 mmol) in DCM (80 mL) was added boron trifluoride etherate (0.5 mL) at 25° C. The resulting mixture was stirred at 25° C. for 3 h, and then washed with aqueous sodium bicarbonate (20 mL) followed by brine (20 mL). The organic layer was dried ($Na_2SO_4$) and concentrated in vacuo to furnish the crude product. Pure compound 14 (7.3 g, 67%) was obtained after purification of crude reaction product by column chromatography (silica gel) using petroleum etherethyl acetate (9:1) as eluent. Colourless syrup; $[\alpha]^{20}_D$=+27.28 (c 1.0, $CHCl_3$); IR ($CHCl_3$): 3436, 3019, 2956, 2876, 1747, 1704, 1605, 1455, 1422, 1358, 1215 cm$^{-1}$; $^1$H NMR (200 MHz, $CDCl_3$): δ 0.84 (d, J=7.3 Hz, 3H), 0.95 (d, J=5.7 Hz, 3H), 1.21-1.39 (m, 3H), 1.43 (s, 3H), 1.56-1.71 (m, 4H), 1.85-2.23 (m, 4H), 2.29-2.43 (m, 2H), 2.58-2.62 (m, 1H), 3.52-3.60 (m, 2H), 3.76 (s, 3H), 4.38-4.54 (m, 2H), 4.79 (d, J=3.5 Hz, 1H), 5.02-5.24 (m, 2H), 5.38 (s, 1H), 7.31-7.36 (m, 5H); (ESI): 568.6 (M+Na)$^+$; HRMS (ESI) m/z for $C_{29}H_{39}NO_9$ [M+Na]$^+$ calcd 568.2510, found: 568.2517.

Example 7: Methyl N-((benzyloxy)carbonyl)-O-((3R,5aS,6R,8aS,9R,10S,12R,12aR)-3,6,9-trimethyl decahydro-12H-3,12-epoxy[1,2]dioxepino[4,3-i] isochromen-10-yl)-L-seryl-L-phenylalaninate (15)

Yield: 63%; colourless syrup; $[\alpha]^{20}_D$=+51.33 (c 1.0, $CHCl_3$); IR ($CHCl_3$): 3428, 3338, 3020, 2929, 2875, 1738, 1718, 1678, 1498, 1377, 1216, 1027 cm$^{-1}$; $^1$H NMR (200 MHz, $CDCl_3$): δ 0.81 (d, J=7.3 Hz, 3H), 0.91 (d, J=5.8 Hz, 3H), 1.11-1.32 (m, 4H), 1.41 (s, 3H), 1.50-1.72 (m, 4H), 1.80-1.96 (m, 2H), 2.22-2.35 (m, 1H), 2.58-2.61 (m, 1H), 3.07-3.15 (m, 2H), 3.69 (s, 3H), 3.71-4.13 (m, 2H), 4.32-4.58 (m, 1H), 4.80 (d, J=4.2 Hz, 1H), 4.74-4.88 (m, 1H), 5.11 (s, 2H), 5.39 (s, 1H), 7.05-7.35 (m, 10H); (ESI): m/z 689.8 (M+Na)$^+$; HRMS (ESI) m/z for $C_{36}H_{46}N_2O_{10}$ [M+Na]$^+$ calcd 689.3043, found: 689.3045.

Example 8: Methyl N-((benzyloxy)carbonyl)-O-((3R,5aS,6R,8aS,9R,10S,12R,12aR)-3,6,9-trimethyl decahydro-12H-3,12-epoxy[1,2]dioxepino[4,3-i] isochromen-10-yl)-L-seryl-L-leucinate (16)

Yield: 58%; colourless syrup; $[\alpha]^{20}_D$=+75.63 (c 0.5, $CHCl_3$); IR ($CHCl_3$): 3416, 3334, 3019, 2955, 2952, 1731, 1682, 1520, 1451, 1215, 1027 cm$^{-1}$; $^1$H NMR (200 MHz, $CDCl_3$): δ 0.85-0.93 (m, 12H), 1.05-1.31 (m, 3H), 1.42 (s, 3H), 1.49-1.72 (m, 5H), 1.79-1.84 (m, 1H), 1.88-1.09 (m, 2H), 2.17-2.65 (m, 4H), 3.71 (s, 3H), 3.78-4.04 (m, 2H), 4.31-4.43 (m, 1H), 4.55-4.66 (m, 1H), 4.83 (d, J=3.3 Hz, 3H), 5.13 (s, 2H), 5.43 (s, 1H), 7.35 (s, 5H); (ESI): m/z 655.3 (M+Na)$^+$; HRMS (ESI) m/z for $C_{33}H_{48}N_2O_{10}$ [M+Na]$^+$ calcd 655.3193, found: 655.3201.

Example 9: Benzyl ((2S)-1-(((E)-3-(diethoxyphos-phoryl)-1-phenylallyl)amino)-1-oxo-3-(((3R,5aS, 6R,8aS,9R,10S,12R,12aR)-3,6,9-trimethyldeca-hydro-12H-3,12-epoxy[1,2]dioxepino[4,3-i]iso-chromen-10-yl)oxy)propan-2-yl)carbamate (1)

Pale yellow syrup; $R_f$=0.34 (MeOH-DCM, 1:19); IR ($CHCl_3$): 3428, 3019, 2929, 1687, 1601, 1496, 1450, 1394, 1216, 1029 cm$^{-1}$; $^1$H NMR (400 MHz, $CDCl^3$): δ 7.39-7.14 (m, 11H), 6.91-6.75 (m, 1H), 5.89-5.76 (m, 1H), 5.76-5.68 (m, 2H), 5.32 (d, J=7.6 Hz, 1H), 5.28 (s, 1H), 5.14-5.03 (m, 2H), 4.80-4.69 (m, 1H), 4.43 (brs, 1H), 4.12-3.91 (m, 5H), 2.60-2.50 (m, 1H), 2.38-2.25 (m, 1H), 2.06-1.90 (m, 3H), 1.87-1.75 (m, 1H), 1.53-1.42 (m, 2H), 1.39-1.35 (m, 4H), 1.31-1.22 (m, 7H), 1.21-1.13 (m, 2H), 0.90-0.85 (m, 3H), 0.76-0.66 (m, 3H); $^{31}$P NMR (202 MHz, $CDCl_3$): δ 17.61; ESI-LCMS: m/z 779.1 (M+Na)$^+$; HRMS (ESI) m/z for $C_{39}H_{53}O_{11}N_2NaP$ (M+Na)$^+$: calcd 779.3279, found 779.3270; HPLC: Chiralpak-IB (0.46 mmØ×250 mmL), 10% IPA in hexane, flow rate 1.0 mL min$^{-1}$, UV detection at 210 nm, $t_R$=15.1 min and $t_R$=17.6 min.

Example 10: Benzyl ((2S)-1-(((2S)-1-(((E)-3-(di-ethoxyphosphoryl)-1-phenylallyl)amino)-1-oxo-3-phenylpropan-2-yl)amino)-1-oxo-3-(((3R,5aS,6R, 8aS,9R,10S,12R,12aR)-3,6,9-trimethyl decahydro-12H-3,12-epoxy[1,2]dioxepino[4,3-i]isochromen-10-yl)oxy)propan-2-yl) carbamate (2)

Colorless solid; $R_f$=0.40 (MeOH-DCM, 1:19); IR ($CHCl_3$): 3422, 2106, 1643, 1217, 1027, 977, 759, 666 cm$^{-1}$; $^1$H NMR (500 MHz, $CDCl_3$): 7.40-7.26 (m, 9H), 7.23-7.15 (m, 4H), 7.15-7.09 (m, 2H), 7.08-6.99 (m, 2H), 6.88-6.72 (m, 2H), 5.85-5.59 (m, 3H), 5.45-5.34 (m, 1H), 5.16-5.05 (m, 1H), 5.04-4.96 (m, 1H), 4.85-4.64 (m, 2H), 4.34-4.22 (m, 1H), 4.13-3.98 (m, 4H), 3.98-3.81 (m, 2H), 3.27-3.12 (m, 1H), 3.03-2.91 (m, 1H), 2.68-2.57 (m, 1H), 2.43-2.29 (m, 1H), 2.10-1.99 (m, 2H), 1.94-1.83 (m, 1H), 1.76-1.66 (m, 1H), 1.66-1.51 (m, 2H), 1.47-1.39 (m, 4H), 1.36-1.24 (m, 8H), 0.97-0.90 (m, 3H), 0.88-0.78 (m, 3H); $^{31}$P NMR (162 MHz, $CDCl_3$): δ 17.76; ESI-LCMS: m/z 926.1 (M+Na)$^+$; HRMS (ESI): m/z calcd for $C_{48}H_{62}O_{12}N_3NaP$ [M+Na]$^+$ 926.3963; found: 926.3947; HPLC: Chiralpak-IA (0.46 mmØ×250 mmL), 18% IPA in hexane, flow rate 1.0 mL min$^{-1}$, UV detection at 210 nm, $t_R$=15.3 min for 2a diastereomer and $t_R$=19.3 min for 2b diastereomer.

Example 11: Benzyl ((S)-1-(((S)-1-(((R,E)-3-(di-ethoxyphosphoryl)-1-phenylallyl)amino)-1-oxo-3-phenylpropan-2-yl)amino)-1-oxo-3-(((3R,5aS,6R, 8aS,9R,10S,12R,12aR)-3,6,9-trimethyl decahydro-12H-3,12-epoxy[1,2]dioxepino[4,3-i]isochromen-10-yl)oxy)propan-2-yl)carbamate (2a)

Colorless solid; $R_f$=0.38 (MeOH-DCM, 1:19); $[\alpha]_D^{24}$ +61.7 (c 1.01, $CHCl_3$); IR ($CHCl_3$): 3418, 3020, 1668, 1505, 1216, 1027, 770, 670 cm$^{-1}$; $^1$H NMR (400 MHz, $CDCl_3$): δ 7.40-7.03 (m, 15H), 6.83-6.69 (m, 2H), 5.76-5.63 (m, 2H), 5.33 (s, 1H), 4.94 (d, J=11.9 Hz, 1H), 4.81-4.70 (m, 2H), 4.67 (d, J=6.0 Hz, 1H), 4.24-4.17 (m, 1H), 4.08-3.96 (m, 4H), 3.91-3.78 (m, 2H), 3.23-3.11 (m, 1H), 2.96-2.89 (m, 1H), 2.64-2.54 (m, 1H), 2.40-2.27 (m, 1H), 2.05-1.94 (m, 2H), 1.89-1.79 (m, 1H), 1.72-1.63 (m, 1H), 1.61-1.51 (m, 1H), 1.45-1.37 (m, 4H), 1.33-1.18 (m, 8H), 0.97-0.87 (m, 3H), 0.85-0.75 (m, 3H); $^{31}$P NMR (162 MHz, $CDCl_3$): δ 17.77; ESI-LCMS: m/z 926.1 (M+Na)$^+$; HRMS (ESI): m/z calcd for $C_{48}H_{62}O_{12}N_3NaP$ [M+Na]$^+$ 926.3963; found: 926.3945; HPLC: de 100% [Chiralpak-IA (0.46 mmØ×250 mmL), 18% IPA in hexane, flow rate 1.0 mL min$^{-1}$, UV detection at 210 nm, $t_R$=15.4 min for 2a diastereomer].

Example 12: Benzyl ((S)-1-(((S,E)-3-(diethoxyphosphoryl)-1-phenylallyl)amino)-1-oxo-3-phenylpropan-2-yl)amino)-1-oxo-3-(((3R,5aS,6R,8aS,9R,10S,12R,12aR)-3,6,9-trimethyl decahydro-12H-3,12-epoxy[1,2]dioxepino[4,3-i]isochromen-10-yl)oxy)propan-2-yl)carbamate (2b)

Colorless solid; $R_f$=0.38 (MeOH-DCM, 1:19); $[\alpha]_D^{24}$ +25.0 (c 1.03, CHCl$_3$); IR (CHCl$_3$): 3424, 3020, 2095, 1641, 1215, 1027, 756, 668 cm$^{-1}$; $^1$H NMR (500 MHz, CDCl$_3$): δ 7.45-7.25 (m, 9H), 7.24-7.01 (m, 7H), 7.01-6.89 (m, 2H), 6.88-6.75 (m, 1H), 5.78-5.68 (m, 2H), 5.43-5.38 (m, 1H), 5.18-5.06 (m, 1H), 5.05-4.93 (m, 1H), 4.79 (d, J=3.4 Hz, 1H), 4.76-4.65 (m, 1H), 4.30 (td, J=4.8, 6.8 Hz, 1H), 4.12-4.00 (m, 4H), 3.99-3.94 (m, 1H), 3.92-3.85 (m, 1H), 3.26-3.13 (m, 1H), 3.03-2.91 (m, 1H), 2.69-2.58 (m, 1H), 2.44-2.31 (m, 1H), 2.10-2.00 (m, 1H), 1.93-1.85 (m, 1H), 1.78-1.68 (m, 1H), 1.66-1.53 (m, 2H), 1.50-1.40 (m, 4H), 1.35-1.25 (m, 8H), 0.95 (d, J=6.5 Hz, 3H), 0.85 (d, J=7.2 Hz, 3H); $^{31}$P NMR (162 MHz, CDCl$_3$): δ 17.65; ESI-LCMS: m/z 926.1 (M+Na)$^+$; HRMS (ESI): m/z calcd for $C_{48}H_{62}O_{12}N_3NaP$ [M+Na]$^+$ 926.3963; found: 926.3950; HPLC: de 100% [Chiralpak-IA (0.46 mmØ×250 mmL), 18% IPA in hexane, flow rate 1.0 mL min$^{-1}$, UV detection at 210 nm, $t_R$=19.1 min for 2b diastereomer].

Example 13: Benzyl ((2S)-1-(((2S)-1-(((E)-3-(diethoxyphosphoryl)-1-phenylallyl)amino)-4-methyl-1-oxopentan-2-yl)amino)-1-oxo-3-(((3R,5aS,6R,8aS,9R,10S,12R,12aR)-3,6,9-trimethyl decahydro-12H-3,12-epoxy[1,2]dioxepino[4,3-i]isochromen-10-yl)oxy)propan-2-yl) carbamate (3)

Colorless solid; $R_f$=0.40 (MeOH-DCM, 1:19); IR (CHCl$_3$): 3422, 2112, 1645, 1217, 1025, 976, 873, 762, 666 cm$^{-1}$; $^1$H NMR (400 MHz, CDCl$_3$): δ 7.46-7.22 (m, 10H), 7.00-6.76 (m, 2H), 5.96-5.68 (m, 3H), 5.48-5.3 (m, 1H), 5.22-4.97 (m, 2H), 4.78 (brs, 1H), 4.60-4.45 (m, 1H), 4.40-4.25 (m, 1H), 4.17-3.79 (m, 6H), 2.63 (brs, 1H), 2.44-2.30 (m, 1H), 2.24-2.10 (m, 2H), 2.09-1.96 (m, 1H), 1.95-1.81 (m, 1H), 1.79-1.65 (m, 2H), 1.64-1.54 (m, 2H), 1.53-1.45 (m, 2H), 1.42 (s, 3H), 1.37-1.21 (m, 8H), 0.97-0.82 (m, 12H); $^{31}$P NMR (162 MHz, CDCl$_3$): δ 17.68; ESI-LCMS: m/z 892.2 (M+Na)$^+$; HRMS (ESI): m/z calcd for $C_{45}H_{64}O_{12}N_3NaP$ [M+Na]$^+$ 892.4120; found: 892.4106; HPLC: Chiralpak-IB (0.46 mmØ×250 mmL), 10% IPA in hexane, flow rate 0.8 mL min$^{-1}$, UV detection at 215 nm, $t_R$=11.4 min for 3a diastereomer and $t_R$=14.2 min for 3b diastereomer.

Example 14: Benzyl ((S)-1-(((S)-1-(((R,E)-3-(diethoxyphosphoryl)-1-phenylallyl)amino)-4-methyl-1-oxopentan-2-yl)amino)-1-oxo-3-(((3R,5aS,6R,8aS,9R,10S,12R,12aR)-3,6,9-trimethyl decahydro-12H-3,12-epoxy[1,2]dioxepino[4,3-i]isochromen-10-yl)oxy)propan-2-yl) carbamate (3a)

Colorless solid; $R_f$=0.38 (MeOH-DCM, 1:19); IR (CHCl$_3$): 3421, 3021, 2402, 2095, 1654, 1508, 1216, 1028, 976, 767, 669 cm$^{-1}$; $^1$H NMR (500 MHz, CDCl$_3$): δ 7.39-7.32 (m, 5H), 7.32-7.26 (m, 5H), 6.97-6.83 (m, 1H), 6.62 (d, J=8.0 Hz, 1H), 5.87 (t, J=17.9 Hz, 1H), 5.76 (brs, 2H), 5.32 (s, 1H), 5.11-4.97 (m, 2H), 4.83-4.75 (m, 1H), 4.58-4.49 (m, 1H), 4.35-4.25 (m, 1H), 4.13-4.01 (m, 4H), 3.90-3.80 (m, 2H), 2.68-2.59 (m, 1H), 2.37 (dt, J=13.9, 3.8 Hz, 1H), 2.09-1.98 (m, 2H), 1.93-1.82 (m, 1H), 1.80-1.66 (m, 2H), 1.65-1.55 (m, 3H), 1.54-1.45 (m, 3H), 1.44-1.40 (m, 3H), 1.35-1.28 (m, 6H), 1.29-1.19 (m, 2H), 0.96-0.82 (m, 12H); $^{31}$P NMR (162 MHz, CDCl$_3$): δ 17.71; ESI-LCMS: m/z 892.2 (M+Na)$^+$; HRMS (ESI): m/z calcd for $C_{45}H_{64}O_{12}N_3NaP$ [M+Na]$^+$ 892.4120; found: 892.4100; HPLC: de 86% [Chiralpak-IB (0.46 mmØ×250 mmL), 10% IPA in hexane, flow rate 0.8 mL min$^{-1}$, UV detection at 215 nm, $t_R$=11.5 min for 3a diastereomer].

Example 15: Benzyl ((S)-1-(((S)-1-(((S,E)-3-(diethoxyphosphoryl)-1-phenylallyl)amino)-4-methyl-1-oxopentan-2-yl)amino)-1-oxo-3-(((3R,5aS,6R,8aS,9R,10S,12R,12aR)-3,6,9-trimethyl decahydro-12H-3,12-epoxy[1,2]dioxepino[4,3-i]isochromen-10-yl)oxy)propan-2-yl) carbamate (3b)

Colorless solid; $R_f$=0.40 (MeOH-DCM, 1:19); IR (CHCl$_3$): 3417, 1639, 1218, 1030, 769, 672 cm$^{-1}$; $^1$H NMR (500 MHz, CDCl$_3$): δ 7.42-7.28 (m, 10H), 6.99-6.79 (m, 2H), 5.94-5.71 (m, 3H), 5.42 (s, 1H), 5.21-5.08 (m, 2H), 4.85-4.76 (m, 1H), 4.56-4.47 (m, 1H), 4.39-4.31 (m, 1H), 4.13-3.89 (m, 6H), 2.69-2.58 (m, 1H), 2.38 (dt, J=13.9, 3.4 Hz, 1H), 2.14-1.97 (m, 2H), 1.96-1.83 (m, 1H), 1.80-1.66 (m, 2H), 1.65-1.46 (m, 5H), 1.43 (s, 3H), 1.34-1.25 (m, 8H), 0.94 (d, J=6.1 Hz, 3H), 0.90-0.87 (m, 6H), 0.87-0.84 (m, 3H); $^{31}$P NMR (162 MHz, CDCl$_3$): δ 17.65; ESI-LCMS: m/z 892.2 (M+Na)$^+$; HRMS (ESI): m/z calcd for $C_{45}H_{64}O_{12}N_3NaP$ [M+Na]$^+$ 892.4120; found: 892.4108; HPLC: de 83% [Chiralpak-IB (0.46 mmØ×250 mmL), 10% IPA in hexane, flow rate 0.8 mL min$^{-1}$, UV detection at 215 nm, $t_R$=15.0 min for 3b diastereomer].

Example 16: Benzyl (2S,4R)-2-(((E)-3-(diethoxyphosphoryl)-1-phenylallyl)carbamoyl)-4-(((3R,5aS,6R,8aS,9R,10S,12R,12aR)-3,6,9-trimethyldecahydro-12H-3,12-epoxy[1,2]dioxepino[4,3-i]isochromen-10-yl)oxy)pyrrolidine-1-carboxylate (4)

Colorless syrup; $R_f$=0.34 (MeOH-DCM, 1:19); $^1$H NMR (400 MHz, CDCl$_3$): δ 7.41-7.06 (m, 10H), 6.93-6.76 (m, 1H), 6.03-5.75 (m, 1H), 5.74-5.63 (m, 1H), 5.39-5.31 (m, 1H), 5.22-5.02 (m, 2H), 4.84-4.71 (m, 1H), 4.54-4.34 (m, 2H), 4.15-3.95 (m, 4H), 3.83-3.61 (m, 1H), 3.43-3.23 (m, 1H), 2.62-2.51 (m, 1H), 2.50-2.39 (m, 1H), 2.38-2.28 (m, 1H), 2.21-2.08 (m, 1H), 2.07-1.93 (m, 2H), 1.91-1.80 (m, 2H), 1.69-1.51 (m, 3H), 1.42-1.37 (m, 3H), 1.34-1.19 (m, 9H), 0.97-0.89 (m, 3H), 0.66 (d, 3H); $^{31}$P NMR (162 MHz, CDCl$_3$): δ 18.02; ESI-LCMS: m/z 805.2 (M+Na)$^+$; HRMS (ESI): m/z for $C_{41}H_{55}O_{11}N_2NaP$ (M+Na)$^+$: calcd 805.3436, found 805.3423.

Example 17: Benzyl (2S,4R)-2-(((2S)-1-(((E)-3-(diethoxyphosphoryl)-1-phenylallyl)amino)-4-methyl-1-oxopentan-2-yl)carbamoyl)-4-(((3R,5aS,6R,8aS,9R,10S,12R,12aR)-3,6,9-trimethyl decahydro-12H-3,12-epoxy[1,2]dioxepino[4,3-i]isochromen-10-yl)oxy)pyrrolidine-1-carboxylate (5)

Colorless solid; $R_f$=0.32 (MeOH-DCM, 1:19); IR (CHCl$_3$): 3419, 3018, 2962, 2402, 1683, 1519, 1418, 1353, 1217, 1101, 1029, 989, 876, 768, 668 cm$^{-1}$; $^1$H NMR (400 MHz, CDCl$_3$): δ 7.52-7.24 (m, 10H), 7.03-6.82 (m, 1H), 6.45 (d, J=7.3 Hz, 1H), 6.03-5.65 (m, 2H), 5.46-5.29 (m, 1H), 5.28-5.07 (m, 1H), 5.06-4.72 (m, 2H), 4.62-4.29 (m, 3H), 4.20-3.95 (m, 4H), 3.82-3.61 (m, 1H), 3.41 (t, J=11.6 Hz, 1H), 2.60 (brs, 1H), 2.44-2.29 (m, 2H), 2.17-1.99 (m, 4H), 1.96-1.76 (m, 2H), 1.72-1.53 (m, 5H), 1.52-1.40 (m, 5H), 1.39-1.21 (m, 9H), 0.97 (d, 3H), 0.94-0.85 (m, 6H), 0.76-0.62 (m, 3H); $^{31}$P NMR (202 MHz, CDCl$_3$): δ 18.01; ESI-LCMS: m/z 918.1 (M+Na)$^+$; HRMS (ESI): m/z calcd for C$_{47}$H$_{66}$O$_{12}$N$_3$NaP [M+Na]$^+$ 918.4276; found: 918.4255; HPLC: Chiralpak-IA (0.46 mmØ×250 mmL), 20% IPA in hexane, flow rate 1.0 mL min$^{-1}$, UV detection at 215 nm, $t_R$=11.8 min for 5b$_β$ and $t_R$=14.8 min for 5b$_α$, and $t_R$=20.6 min for 5a$_α$ and $t_R$=31.2 min for 5a$_β$.

Example 18: Benzyl (2S,4R)-2-(((S)-1-(((R,E)-3-(diethoxyphosphoryl)-1-phenylallyl)amino)-4-methyl-1-oxopentan-2-yl)carbamoyl)-4-(((3R,5aS,6R,8aS,9R,10S,12R,12aR)-3,6,9-trimethyl decahydro-12H-3,12-epoxy[1,2]dioxepino[4,3-i]isochromen-10-yl)oxy)pyrrolidine-1-carboxylate (5a)

Colorless solid; R$_f$=0.30 (MeOH-DCM, 1:19); IR (CHCl$_3$): 3420, 3339, 3018, 2963, 2878, 2402, 1684, 1516, 1418, 1352, 1216, 1099, 1029, 989, 876, 771, 669 cm$^{-1}$; $^1$H NMR (500 MHz, CDCl$_3$): δ 7.44-7.22 (m, 10H), 6.92 (t, J=18.3 Hz, 1H), 6.50-6.33 (m, 1H), 5.92 (t, J =17.5 Hz, 1H), 5.80 (brs, 1H), 5.42-5.28 (m, 1H), 5.05-4.93 (m, 1H), 4.90-4.71 (m, 2H), 4.49 (brs, 2H), 4.41-4.26 (m, 1H), 4.14-4.00 (m, 4H), 3.94-3.59 (m, 1H), 3.44-3.33 (m, 1H), 2.65-2.54 (m, 1H), 2.43-2.26 (m, 2H), 2.18-1.78 (m, 5H), 1.71-1.48 (m, 5H), 1.47-1.40 (m, 4H), 1.36-1.20 (m, 9H), 0.97 (brs, 3H), 0.94-0.87 (m, 6H), 0.67 (brs, 3H); $^{31}$P NMR (162 MHz, CDCl$_3$): δ 18.05; ESI-LCMS: m/z 918.1 (M+Na)$^+$; HRMS (ESI): m/z calcd for C$_{47}$H$_{66}$O$_{12}$N$_3$NaP [M+Na]$^+$ 918.4276; found: 918.4257; HPLC: Chiralpak-IA (0.46 mmØ×250 mmL), 20% IPA in hexane, flow rate 1.0 mL min$^{-1}$, UV detection at 215 nm, $t_R$=20.1 min for 5a$_α$, and $t_R$=29.6 min for 5a$_β$.

Example 19: Benzyl (2S,4R)-2-(((S)-1-(((S,E)-3-(diethoxyphosphoryl)-1-phenylallyl)amino)-4-methyl-1-oxopentan-2-yl)carbamoyl)-4-(((3R,5aS,6R,8aS,9R,10S,12R,12aR)-3,6,9-trimethyl decahydro-12H-3,12-epoxy[1,2]dioxepino[4,3-i]isochromen-10-yl)oxy)pyrrolidine-1-carboxylate (5b)

Colorless solid; R$_f$=0.32 (MeOH-DCM, 1:19); IR (CHCl$_3$): 3420, 3019, 2964, 2402, 1682, 1519, 1419, 1353, 1216, 1099, 1029, 989, 876, 769, 670 cm$^{-1}$; $^1$H NMR (500 MHz, CDCl$_3$): δ 7.47-7.34 (m, 7H), 7.33-7.28 (m, 3H), 6.93 (t, J=18.3 Hz, 1H), 6.79-6.64 (m, 1H), 5.92-5.68 (m, 2H), 5.40 (brs, 1H), 5.30-5.09 (m, 2H), 4.80 (brs, 1H), 4.62-4.33 (m, 3H), 4.20-3.96 (m, 4H), 3.95-3.62 (m, 1H), 3.44 (d, J=10.7 Hz, 1H), 2.61 (brs, 1H), 2.50-2.14 (m, 3H), 2.12-1.75 (m, 4H), 1.74-1.53 (m, 5H), 1.53-1.38 (m, 5H), 1.37-1.19 (m, 9H), 0.98 (d, 3H), 0.95-0.91 (m, 3H), 0.90-0.86 (m, 3H), 0.71 (d, 3H); $^{31}$P NMR (162 MHz, CDCl$_3$): δ 17.96; ESI-LCMS: m/z 918.2 (M+Na)$^+$; HRMS (ESI): m/z calcd for C$_{47}$H$_{66}$O$_{12}$N$_3$NaP [M]$^+$918.4276; found: 918.4258; HPLC: Chiralpak-IA (0.46 mmØ×250 mmL), 20% IPA in hexane, flow rate 1.0 mL min$^{-1}$, UV detection at 215 nm, $t_R$=11.3 min for 5b$_β$ and $t_R$=14.1 min for 5b$_α$.

Example 20: Benzyl (2S,4R)-2-(((2S)-1-(((E)-3-(diethoxyphosphoryl)-1-phenylallyl)amino)-1-oxo-3-phenylpropan-2-yl)carbamoyl)-4-(((3R,5aS,6R,8aS,9R,10S,12R,12aR)-3,6,9-trimethyl decahydro-12H-3,12-epoxy[1,2]dioxepino[4,3-i]isochromen-10-yl)oxy)pyrrolidine-1-carboxylate (6)

Colorless syrup; IR (CHCl$_3$): 3409, 3368, 3018, 2957, 2876, 1682, 1497, 1455, 1416, 1358, 1216, 1030 cm$^{-1}$; $^1$H NMR (200 MHz, CDCl$_3$): δ 7.17-7.30 (m, 15H), 6.75-6.94 (m, 1H), 5.71-5.93 (m, 2H), 4.80-5.30 (m, 2H), 4.73-4.90 (m, 2H), 4.27-4.39 (m, 2H), 3.96-4.13 (m, 2H), 3.57-4.13 (m, 2H), 3.13-3.33 (m, 2H), 2.27-2.57 (m, 3H), 1.85-1.99 (m, 3H), 1.49-1.70 (m, 3H), 1.42 (s, 3H), 1.22-1.32 (m, 10H), 0.94 (d, 3H), 0.63 (d, 3H); $^{31}$P NMR (162 MHz, CDCl$_3$): δ 18.21; ESI-LCMS: m/z 953.2 (M+Na)$^+$.

Example 21: Antimalarial Activity Protocol a) Expression and Purification of Recombinant Falcpain-2 Enzyme:

Recombinant falcipain-2 was prepared according to the method described by Shenai et al. (*J Biol Chem.;* 2000, 275(37): 29000-10) and Kumar et al. (*Biochem Biophys. Res Commun.* 2004, 317(1), 38-45) with slight modification. Briefly, *Escherichia coli* M15 containing pQE30-FP-2 plasmid were grown to mid-log phase and induced with isopropyl-1-thio-b-D-galactopyranoside (IPTG, 0.5 mM) for 5 h at 37° C. Cells were harvested, washed with ice-cold 100 mM Tris-Cl, 10 mM EDTA, pH 7.4, sonicated (12 cycles of 10 s each, with cooling for 10 s between the cycles), and centrifuged at 15,000 rpm for 45 min at 4° C. The pellet was washed twice with 2.5 M urea, 20 mM Tris-Cl 2.5% Triton X-100, pH 8.0; centrifuged at 15,000 rpm for 45 min at 4° C.; and solubilized in 6 M guanidine HCl, 20 mM Tris-Cl, 250 mM NaCl, 20 mM imidazole, pH 8.0 (5 ml/g of inclusion body pellet) at RT for 60 min with gentle stirring. Insoluble material was separated by centrifuging at 15,000 rpm for 60 min at 4° C. For the purification of the recombinant protein, the supernatant was incubated overnight at 4° C. with a nickel-nitrilotriacetic acid (Ni-NTA) resin. The resin was loaded on a column and washed with 10 bed volumes each of 6 M guanidine HCl, 20 mM Tris-Cl, 250 mM NaCl, pH 8.0; 8 M urea, 20 mM Tris-Cl, 500 mM NaCl, pH 8.0; and 8 M urea, 20 mM Tris-Cl, 30 mM imidazole, pH 8.0. Bound protein was eluted with 8 M urea, 20 mM Tris-Cl, 1 M imidazole, pH 8.0 and quantified by the Biocinchoninic acid assay. For the refolding, the fractions containing falcipain-2 protein were pooled in ice-cold refolding buffer: 100 mM diluted in Tris-Cl, 1 mM EDTA, 20% glycerol, 250 mM L-arginine, 1 mM GSH, 1 mM GSSG, pH 8.0 was added in a 100 fold dilution. The mixture was incubated with moderate stirring at 4° C. for 24 h, and concentrated to 25 ml using a stirred cell with a 10-kDa cut-off membrane (Pellicon XL device, Millipore) at 4° C. The sample was then filtered using a 0.22-mm syringe filter. The purified and concentrated protein was quantified using Biocinchoninic acid assay.

b) Fluorometric Assay for Falcipain-2 activity:

For screening of falcipain-2 inhibitors, a 96-well plate fluorometric assay was developed following a protocol described by Kumar et al. (*Biochem Biophys Res Commun.;* 2004, 317(1), 38-45) Briefly, reaction was set up in a 200 ml reaction mixture containing 100 mM NaOAc, 10 mM DTT, 6 mg enzyme and different concentrations of inhibitors, pH 5.5. 10 mM of fluorogenic substrate benzyloxycarbonyl-Phe-Arg-7-amino-4-methylcoumarin hydrochloride (ZFR- AMC) was added, and the release of 7-amino-4-methylcoumarin (AMC) was monitored (excitation 355 nm; emission 460 nm) over 30 min at RT in Perkin Elmer Victor3 multi-label counter. Activities were compared as fluorescence released over time in assay without or with different concentration of each compound tested. The $IC_{50}$ values were calculated from curve fittings by software Workout V 2.5. $K_i$ values were derived from the Cheng-Prusoff equation $$K_i = \frac{IC_{50}}{1 + \left(\frac{[S]}{K_M}\right)}$$

relating both parameters when substrate concentration and $K_M$ are known:

c) Expression and Activity of Heme Detoxification Protein (HDP)

Briefly, cultures of E. coli M15 cells containing plasmid pHDP (HDP gene cloned in pQE expression vector) were grown to mid-log phase, induced with IPTG (1 mM) for 4 h at 37° C., and harvested by centrifugation at 4,000×g for 20 min. The total cell pellet was resuspended in wash buffer (50 mM Tris-HCl at pH 7.5, 20 mM EDTA) containing 0.5 mg/mL lysozyme and incubated for 1 h at room temperature with intermittent shaking, and then with vigorous shaking for an additional 30 min. The washed cell pellet was lysed after adding wash buffer containing 0.5 M NaCl and 2.5% Triton X-100. The inclusion bodies were pelleted by centrifugation at 13,000 rpm for 50 min at 4° C., resuspended in wash buffer containing 1% Triton X-100 using a sonicator, pelleted again, and then washed four times in wash buffer without Triton X-100. The inclusion bodies were solubilized for 30 min in 50 mM CAPS buffer at pH 11.0 containing 1.5% N-lauryl sarcosine and 0.3 M NaCl and centrifuged at 10,000×g for 30 min. The protein was purified from the supernatant using a His-Trap, a high-performance nickel affinity column (GE Health Care) by an imidazole gradient in 50 mM CAPS at pH 11.0 containing 0.3% N-lauryl sarcosine and 0.3 M NaCl. Protein-containing fractions were pooled and dialyzed against 25 mM CAPS buffer (pH 11.0) containing 135 mM NaCl. The activity of the protein was assessed by its ability to convert heme to hemozoin (Hz) (Jani et al 2008).

d) In Vitro Hz Formation Assay

The in vitro hemzoin formation assay were carried out in 1 ml reaction buffered with 500 mM sodium acetate at pH 5.2 with 5 mM reduced glutathione containing heme (300 µM) and 0.5 µM recombinant HDP, the reaction was carried out at 37 C for 3 h. Subsequently, free heme in the reaction was removed by repeated washing of the pellet with 2.5% SDS and 0.1M sodium bicarbonate (pH 9.1) followed by repeated washing with distilled water until no soluble heme was visible in the supernatant. The Hz pellet was resuspended in 1 ml of 0.1 N NaOH, and absorbance was measured at 400 nm, heme concentration was calculated from standard curve. Heme stock (10 mM) was prepared by dissolving 3.3 mg of hemin (Sigma) in 500 µl of 1 M NaOH, which was used to make dilutions ranging from 50 µm-600 µm to plot the standard curve. A reaction containing buffered heme alone was used as negative control. To assess the effect of different compounds on hemozoin formation, the assay was performed in presence of the compounds at various concentrations.

e) P. falciparum Growth Inhibition Assay

P. falciparum strain 3D7, Dd2 and 7G8 were cultured in RPMI media (Invitrogen) supplemented with 0.5% albumax and 4% haematocrit using a protocol described previously [Trager and Jensen (Science,1976; 193:673-675)]. Cultures were synchronized by repeated sorbitol treatment following Lambros and Vanderberg (J Parasitol; 1979; 65:418-420). Each growth inhibition assay was performed in triplicate and the experiment was repeated twice. Each well contained 0.5 ml of complete media [RPMI (invitrogen) with 0.5% albumax], 4% haematocrit and the parasitaemia adjusted to ~1%; the compound added to the parasite cultures to desired final concentrations (0-100 □M) and same amount of solvent (DMSO) was added to the control wells. The cultures were allowed to grow further for 48 h. Parasite growth was assessed by DNA fluorescent dye-binding assay using SYBR green (Sigma) following Smilkstein et al (Antimicrob Agents Chemother.; 2004, 48, 1803-1806).

f) In Vitro Toxicity Assay on CHO Cells

Cytotoxicity assay was carried out using the CHO cells proliferation test. CHO cells were seeded in triplicates at 100 µL aliquots ($1\times10^4$ cells per well) with DMEM medium in Nunclon flat bottom 96-well plates and were allowed to grow for 24 h. Subsequently, the medium was replaced by test medium containing each inhibtor (0-500 µM), or DMSO as control. The CHO cells were allowed to grow for further 24 h, and then 10 µl of the WST-1 reagent was added and plates were incubated for 30 min. The plates were read at 450 nm absorption and 630 nm reference wavelength using a TECAN GENios Pro microplate reader. The percentage growth was calculated by comparing with the control set. The $EC_{50}$ values for each compound were calculated from the growth inhibition curve.

g) In Vivo Parsiticidal Assays with P. berghei Mice Malaria Model

Five groups of female BALB/c mice, 6-8 weeks of age (four mice/group) were used for testing the in vivo parsiticidal and protective efficacy of different drug treatments. Mice were injected IP with $1\times10^6$ P. berghei infected erythrocytes. The drug treatment was initiated 5 days after inducing parasitemia; mice in a group were given 4 doses of a compound at 12.5 mg/Kg of body weight. Control mice were given solvent alone. The parasitemia was assessed everyday in thin smears of Giemsa stained RBCs from tail blood of each mouse, by counting parasitized erythrocytes in more than 10,000 erythrocytes. Time of death of the mice in each group was also monitored.

Advantages of the Invention

The present invention provides a new artemisinin-dipeptidyl vinyl based compound of Formula (I) which has two distinct mode of action which comprises: (i) inhibition of falcipain-2, a major hemoglobinase in the parasite and (ii) inhibition of polymerization of free heme to hemozoin.

These molecules are very effective in vitro and in vivo parasiticidal activity.

These compounds of Formula (I) have higher parsiticidal efficacies as compared to artemisinin alone.

The compounds of Formula (I) may be used as anticancer and anti HIV agents.

The invention claimed is:

1. A compound of Formula (I) or a pharmaceutically acceptable salt thereof,

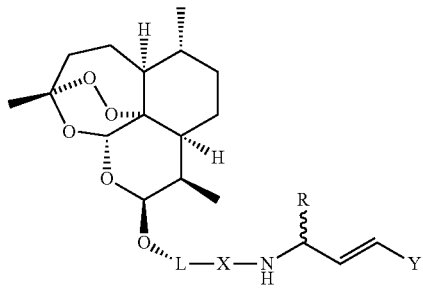

Formula (I)

Wherein, 'L' is Linker selected from group consisting of

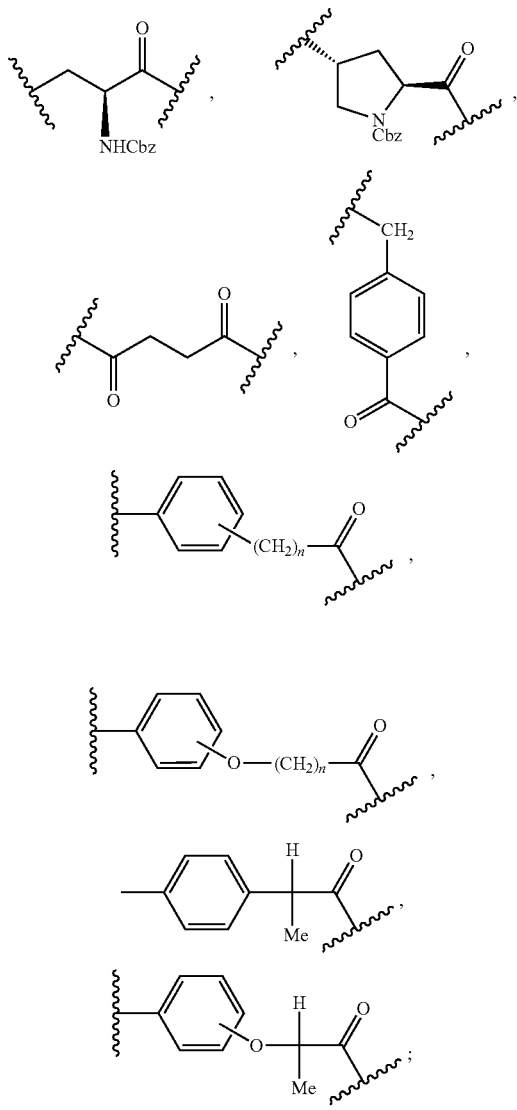

X is selected from the hydrogen, —CO—, —CONHCHRCO—;

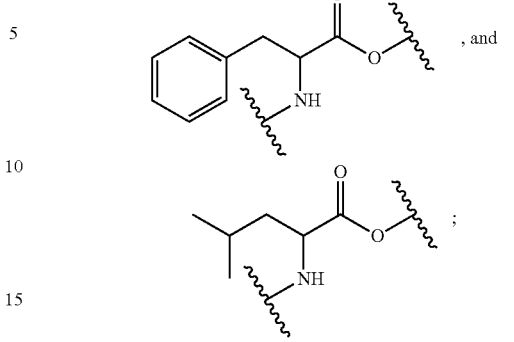

R is selected from the group consisting of hydrogen, alkyl, aryl, alkyl aryl, haloalkyl, alkoxy, hydroxy, halo, cyano, heteroaryl, alkyl heteroaryl, alkenyl, alkenyl aryl, alkenyl heteroaryl, alkynyl, alkynyl aryl, alkynyl heteroaryl, cycloalkyl, heterocycloalkyl, alkyl cycloalkyl, alkyl heterocycloalkyl, alkyl carboxy, acyl, alkyl acyl, alkyl acyloxy, alkyl alkoxy, alkoxycarbonyl, alkyl alkoxycarbonyl, aminocarbonyl, alkyl aminocarbonyl, alkyl acylamino, alkyl ureido, amino, alkyl amino, sulfonyloxy, alkyl sulfonyloxy, sulfonyl, alkyl sulfonyl, sulfinyl, alkyl sulfinyl, alkyl sulfanyl and alkyl sulfonylamino;

Y is —PO (OR$_1$)$_2$, wherein R$_1$ is selected from the group consisting of alkyl or aryl and alkyl aryl.

2. The compounds of Formula (I) as claimed in claim 1, wherein said compounds are selected from the group consisting of:

i) Benzyl ((2S)-1-(((E)-3-(diethoxyphosphoryl)-1-phenylallyl)amino)-1-oxo-3-(((3R,5aS,6R, 8aS,9R,10S,12R,12aR)-3,6,9-trimethyldecahydro-12H-3,12-epoxy[1,2]dioxepino[4,3-i]isochromen-10-yl)oxy)propan-2-yl)carbamate (1);

ii) Benzyl ((2S)-1-(((2S)-1-(((E)-3-(diethoxyphosphoryl)-1-phenylallyl)amino)-1-oxo-3-phenylpropan-2-yl) amino)-1-oxo-3-(((3R,5aS,6R,8aS,9R,10S,12R,12 aR)-3,6,9-trimethyldeca hydro-12H-3,12-epoxy[1,2] dioxepino[4,3-i]isochromen-10-yl)oxy)propan-2-yl) carbamate (2);

iii) Benzyl ((S)-1-(((S)-1-(((R,E)-3-(diethoxyphosphoryl)-1-phenylallyl)amino)-1-oxo-3-phenylpropan-2-yl) amino)-1-oxo-3-(((3R,5aS,6R,8aS,9R,10S,12R,12aR)-3,6,9-trimethyldeca hydro-12H-3,12-epoxy[1,2] dioxepino[4,3-i]isochromen-10-yl)oxy)propan-2-yl) carbamate (2a);

iv) Benzyl ((S)-1-(((S)-1-(((S,E)-3-(diethoxyphosphoryl)-1-phenylallyl)amino)-1-oxo-3-phenylpropan-2-yl) amino)-1-oxo-3-(((3R,5aS,6R,8aS,9R,10S,12R,12aR)-3,6,9-trimethyldeca hydro-12H-3,12-epoxy[1,2] dioxepino[4,3-i]isochromen-10-yl)oxy)propan-2-yl) carbamate (2b);

v) Benzyl ((2S)-1 -(((2S)-1-(((E)-3-(diethoxyphosphoryl)-1-phenylallyl)amino)-4-methyl-1-oxopentan-2-yl) amino)-1-oxo-3-(((3R,5aS,6R,8aS,9R,10S,12R,12aR)-3,6,9-trimethyldeca hydro-12H-3,12-epoxy[1,2] dioxepino[4,3-i]isochromen-10-yl)oxy)propan-2-yl) carbamate (3);

vi) Benzyl ((S)-1-(((S)-1-(((R,E)-3-(diethoxyphosphoryl)-1-phenylallyl)amino)-4-methyl-1-oxopentan-2-yl) amino)-1-oxo-3-(((3R,5 aS,6R,8aS,9R,10S,12R,12 aR)-3,6,9-trimethyldeca hydro-12H-3,12-epoxy[1,2] dioxepino[4,3-i]isochromen-10-yl)oxy)propan-2-yl) carbamate (3a);

vii) Benzyl ((S)-1-(((S)-1-(((S,E)-3-(diethoxyphosphoryl)-1-phenylallyl)amino)-4-methyl-1-oxopentan-2-yl)amino)-1-oxo-3-(((3R,5aS,6R,8aS,9R,10S,12R,12aR)-3,6,9-trimethyldeca hydro-12H-3,12-epoxy[1,2]dioxepino[4,3-i]isochromen-10-yl)oxy)propan-2-yl) carbamate (3b);

viii) Benzyl (2S,4R)-2-(((E)-3-(diethoxyphosphoryl)-1-phenylallyl)carbamoyl)-4-(((3R,5aS, 6R,8aS,9R,10S, 12R,12aR)-3,6,9-trimethyldecahydro-12H-3,12-epoxy[1,2]dioxepino[4,3-i]isochromen-10-yl)oxy) pyrrolidine-1-carboxylate (4);

ix) Benzyl (2S,4R)-2-(((2S)-1-(((E)-3-(diethoxyphosphoryl)-1-phenylallyl)amino)-4-methyl-1-oxopentan-2-yl)carbamoyl)-4-(((3R,5aS,6R,8aS,9R,10S,12R,12aR)-3,6,9-trimethyldeca hydro-12H-3,12-epoxy[1,2]dioxepino[4,3-i]isochromen-10-yl)oxy)pyrrolidine-1-carboxylate (5);

x) Benzyl (2S,4R)-2-(((S)-1-(((R,E)-3-(diethoxyphosphoryl)-1-phenylallyl)amino)-4-methyl-1-oxopentan-2-yl)carbamoyl)-4-(((3R,5aS,6R,8aS,9R,10S,12R,12aR)-3,6,9-trimethyldeca hydro-12H-3,12-epoxy[1,2]dioxepino[4,3-i]isochromen-10-yl)oxy)pyrrolidine-1-carboxylate (5a);

xi) Benzyl (2S,4R)-2-(((S)-1-(((S,E)-3 -(diethoxyphosphoryl)-1-phenylallyl)amino)-4-methyl-1-oxopentan-2-yl)carbamoyl)-4-(((3R,5aS,6R,8aS,9R,10S,12R,12aR)-3,6,9-trimethyldeca hydro-12H-3,12-epoxy[1,2]dioxepino[4,3-i]isochromen-10-yl)oxy)pyrrolidine-1-carboxylate (5b);

xii) Benzyl (2S,4R)-2-(((2S)-1-(((E)-3-(diethoxyphosphoryl)-1-phenylallyl)amino)-1-oxo-3 -phenylpropan-2-yl)carbamoyl)-4-(((3R,5aS,6R,8aS,9R,10S,12R,12aR)-3,6,9-trimethyl decahydro-12H-3,12-epoxy[1,2]dioxepino[4,3-i]isochromen-10-yl)oxy)pyrrolidine-1-carboxylate (6).

3. A process for the preparation of compound of Formula (I), as claimed in claim 1, wherein the process comprises the following steps:

a) adding Lewis acid to a solution of compound of Formula 12 in a dichloromethane and a compound that forms linker 'L' in a dichloromethane at 27° C. for the period of 6 hr to afford linker attached artemisinin compounds;

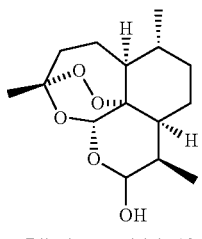

Dihydroartemisinin 12 b) hydrolyzing the ester of linker attached artemisinin compounds obtained from step a) to free acid by adding aqueous solution of LiOH in tetrahydrofuran at temperature in the range of 27° C. with constant stirring to afford the corresponding artemisinin free acid compound;

c) subjecting the free acid compound obtained from step (b) to peptide coupling reaction with alkyl ester of phenylalanine or alkyl ester of leucine in the presence of coupling reagent N,N'-Dicyclohexylcarbodiimide (DCC) and Hydroxybenzotriazole (HOBt) in tetrahydrofuran at 0° C. for 1 hr followed by at 25° C. for 1 hr to afford corresponding dipeptide;

d) subjecting the free acid compound obtained from step (b) or dipeptide of step (c) to peptide coupling reaction with γ-amino vinyl phosphonate compounds in the presence of coupling regents N,N'-Dicyclohexylcarbodiimide (DCC) and Hydroxybenzotriazole (HOBt) in in tetrahydrofuran at 0° C. for 1 hr followed by at 25° C. for 1 hr to afford artemisinin-dipeptidyl vinyl based compound of Formula (I).

4. The process as claimed in claim 3, wherein the Lewis acid is selected from the group comprising of Boron trifluoride diethyl etherate ($BF_3.Et_2O$), Silicon tetrabromide ($SiBr_4$), Silicon tetrafluoride ($SiF_4$) or Aluminium fluoride ($AlF_3$).

5. The process as claimed in claim 3, wherein the compound that forms linker 'L' is selected from compound of Formula 8 or compound of Formula 10:

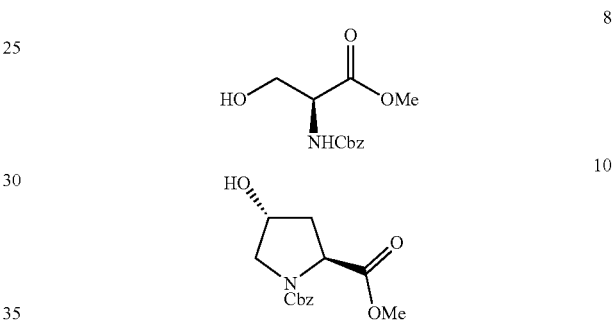

such that the linker is

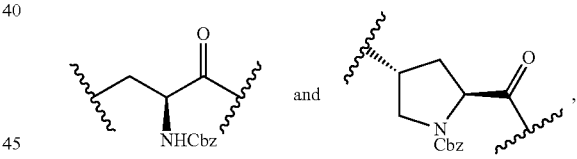

respectively.

6. The process as claimed in claim 3, wherein said alkyl ester of phenylalanine is selected from methyl ester of phenylalanine ($NH_2$-Phe-OMe) or ethyl ester of phenylalanine ($NH_2$-Phe-OEt) and the alkyl ester of leucine is selected from methyl ester of leucine ($NH_2$-Leu-OMe) or ethyl ester of leucine ($NH_2$-Leu-OEt).

7. A pharmaceutical composition comprising a compound of Formula (I) as claimed in claim 1, or a pharmaceutically acceptable salt thereof, and a pharmaceutically acceptable carrier, diluent or excipient.

8. The pharmaceutical composition as claimed in claim 7, wherein said pharmaceutical composition is applicable for the treatment against growth of malarial parasite (*Plasmodium falciparum*).

* * * * *